United States Patent
Küster et al.

(10) Patent No.: US 11,657,120 B2
(45) Date of Patent: May 23, 2023

(54) METHOD AND APPARATUS FOR DETERMINING A SMOOTHED DATA POINT WITHIN A STREAM OF DATA POINTS

(71) Applicant: EyeSense AG, Basel (CH)

(72) Inventors: Frank Küster, Miltenberg (DE);
Roland Krivànek, Aschaffenburg (DE);
Achim Müller, Grossostheim (DE)

(73) Assignee: EyeSense AG, Basel (CH)

( * ) Notice: Subject to any disclaimer, the term of this patent is extended or adjusted under 35 U.S.C. 154(b) by 770 days.

(21) Appl. No.: 16/664,133

(22) Filed: Oct. 25, 2019

(65) Prior Publication Data

US 2020/0125627 A1 Apr. 23, 2020

Related U.S. Application Data

(63) Continuation of application No. 14/911,673, filed as application No. PCT/EP2014/066706 on Aug. 4, 2014, now abandoned.

(30) Foreign Application Priority Data

Aug. 14, 2013 (EP) ..................................... 13180412

(51) Int. Cl.
*G01N 33/48* (2006.01)
*G06F 17/17* (2006.01)
(Continued)

(52) U.S. Cl.
CPC ............ *G06F 17/17* (2013.01); *A61B 5/0022* (2013.01); *A61B 5/0205* (2013.01); *A61B 5/333* (2021.01);
(Continued)

(58) Field of Classification Search
None
See application file for complete search history.

(56) References Cited

U.S. PATENT DOCUMENTS

| 2007/0020181 A1* | 1/2007 | Workman | A61B 5/415 |
| | | | 424/9.1 |
| 2008/0167841 A1 | 7/2008 | Ramsey et al. | |
| 2013/0060107 A1* | 3/2013 | Crane | G01N 33/66 |
| | | | 600/316 |

OTHER PUBLICATIONS

Roark, Dennis E. "Reverse Smoothing: a model-free data smoothing algorithm." Biophysical chemistry 108.1-3 (2004): 121-126.*
(Continued)

*Primary Examiner* — Anna Skibinsky
(74) *Attorney, Agent, or Firm* — Taft Stettinius & Hollister LLP

(57) ABSTRACT

A method and an apparatus for determining at least one smoothed data point $(t_k, s_k)$ within a stream of data points $\{t_i, s_i\}$ with $1 \leq i \leq z$, $k < z$ is disclosed. Herein, the stream of data points $\{t_i, s_i\}$ is consecutively acquired in a manner that a data point $(t_i, s_i)$ is acquired after an acquisition of a preceding data point $(t_{i-1}, s_{i-1})$, wherein each data point $(t_i, s_i)$ comprises a valid value or an invalid value or a missing value for the signal $s_i$ at a time $t_i$. Herein, the signal $s_i$ at the time $t_i$ comprises physical, chemical, biological, environmental, and/or technical data acquired by means of a technical set-up. According to the method, a set of data points is provided, wherein for each smoothed data point $(t_k, s_k)$ a smoothing set is created. For each smoothed data point $(t_k, s_k)$, trailing data resulting from large gaps are removed until it is verified whether the smoothing set comprises a minimal number of data points. Thereafter, for each smoothed data point $(t_k, s_k)$ an initial slope set is calculated, on which at least one exponential smoothing is applied, in which cause an at least once modified slope set is determined. By integrating the at least once modified slope set, a value for the smoothed data point $(t_k, s_k)$ is determined and returned. The method provides a good degree of smoothing without introducing any lag time and with minimal distortions, and is capable of reporting derivatives for the set of smoothed data points at the same time. The method is particularly suited in real-time or nearly real-time measurements which may comprise large gaps within the stream of data points.

20 Claims, 4 Drawing Sheets

Figure 1:
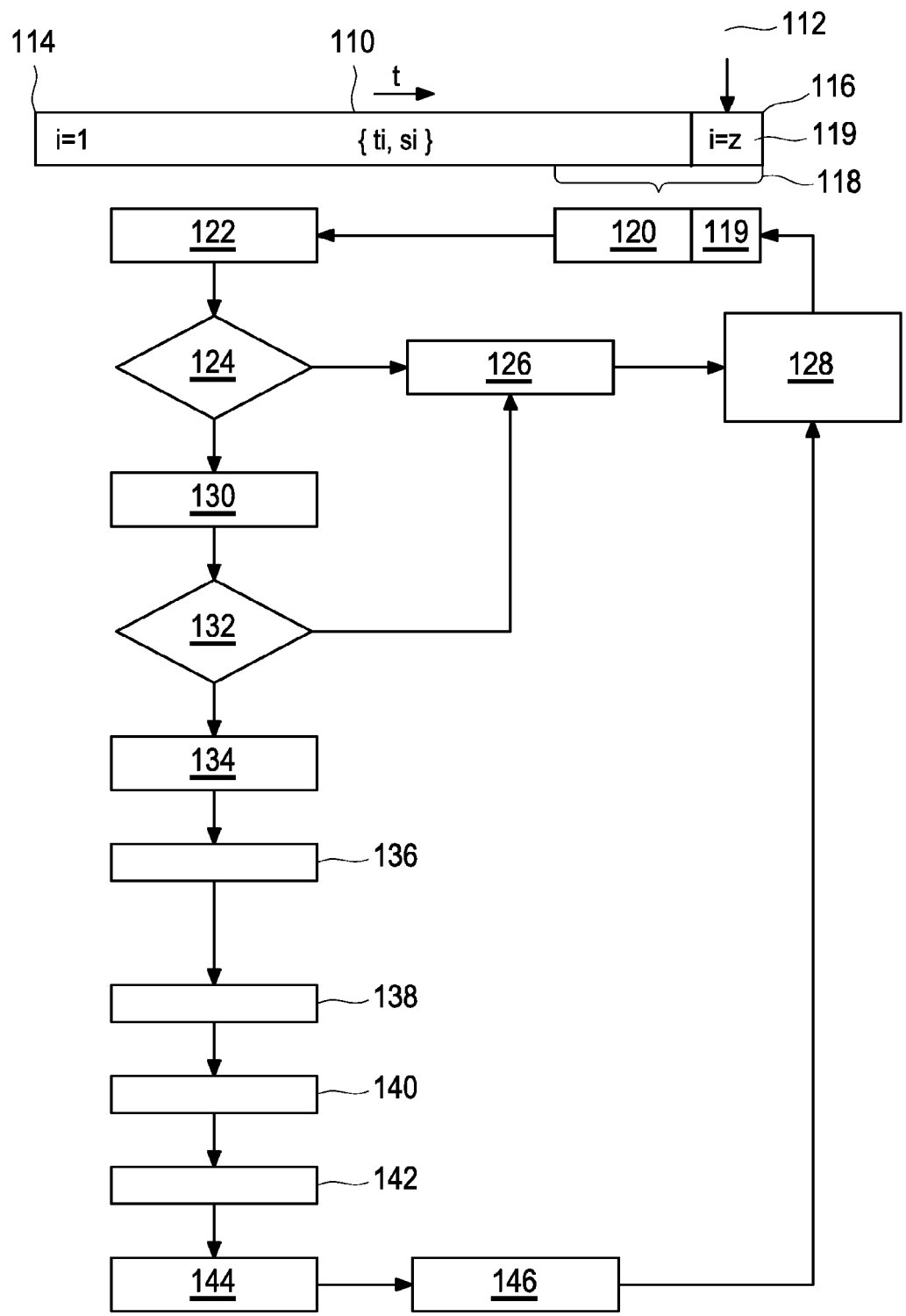

(51) Int. Cl.

| | |
|---|---|
| *G16H 50/50* | (2018.01) |
| *A61B 5/00* | (2006.01) |
| *G06F 17/18* | (2006.01) |
| *A61B 5/333* | (2021.01) |
| *A61B 5/369* | (2021.01) |
| *A61B 5/0205* | (2006.01) |
| *A61B 5/145* | (2006.01) |
| *A61B 5/021* | (2006.01) |
| *A61B 5/024* | (2006.01) |
| *A61B 5/318* | (2021.01) |

(52) U.S. Cl.
CPC ............... *A61B 5/369* (2021.01); *A61B 5/72* (2013.01); *A61B 5/7203* (2013.01); *A61B 5/7221* (2013.01); *G06F 17/18* (2013.01); *G16H 50/50* (2018.01); *A61B 5/0002* (2013.01); *A61B 5/021* (2013.01); *A61B 5/024* (2013.01); *A61B 5/14532* (2013.01); *A61B 5/318* (2021.01)

(56) References Cited

OTHER PUBLICATIONS

Rebrin et al., "Subcutaneous Glucose Predicts Plasma Glucose Independent of Insulin: Implications for Continuous Monitoring", The American Journal of Physiology 277, No. 3 Pt 1 (Sep. 1999): E561-571.

Roark, "Reverse Smoothing: a model-free data smoothing algorithm", Biophysical Chemistry 108, pp. 121-126 (2004).

Holt, "Forecasting seasonals and trends by exponentially weighted moving averages", International Journal of Forecasting 20 (2004) pp. 5-10 (2004). (reprint of an original article from 1957.).

Bequette, "Continuous Glucose Monitoring: Real-time Algorithms for Calibrating, Filtering, and Alarms", Journal of Diabetes Science and Technology 4, No. 2, pp. 404-418 (2010).

Facchinetti et al., "An Online Selt-tunable Method to Denoise CGM Sensor Data", IEEE Transactions on Bio-medical Engineering 57, No. 3, pp. 634-641 (2010).

Iancu et al., "Predictive Blood Glucose Control Using Exponential Smoothing Method", Annals of the University of Craiova, vol. 8 (36), No. 2, pp. 1-6, (2011).

Clarke et al., "Clinical Requirements for Closed-Loop Control Systems", Journal of Diabetes Science and Technology 6, No. 2, pp. 444-452 (2012).

Haworth et al., "Non-parametric regression for space-time forecasting under missing data", Computers, Environment and Urban Systems, vol. 36, No. 6, pp. 538-550 (2012).

Keenan et al., "Interstitial Fluid Glucose Time-lag Correction for Real-time Continuous Glucose Monitoring", Biomedical Signal Processing and Control 8, No. 1, pp. 81-89 (2013).

International Search Report and Written Opinion issued in related International Patent Application No. PCT/EP2014/0666706, completed Aug. 28, 2014.

International Preliminary Report on Patentability issued in related International Patent Application No. PCT/EP2014/0666706, dated Dec. 21, 2015.

\* cited by examiner

METHOD AND APPARATUS FOR DETERMINING A SMOOTHED DATA POINT WITHIN A STREAM OF DATA POINTS

CROSS-REFERENCE TO RELATED APPLICATIONS

The present application is a continuation of U.S. patent application Ser. No. 14/911,673 filed on Feb. 11, 2016, which is a U.S. National Phase of International Patent Application Serial No. PCT/EP2014/066706 filed on Aug. 4, 2014, which claims priority to European Patent Application No. 13180412.2 filed on Aug. 14, 2013. The contents of each of these applications are incorporated herein by reference in their entirety.

FIELD OF THE INVENTION

The present application relates to a method and to an apparatus for determining at least one smoothed data point within a stream of data points. In a further aspect of the invention, the application relates to a use of the apparatus. In a further aspect of the invention, the application refers to a computer program. In a further aspect of the invention, the application refers to a data carrier having a data structure stored thereon.

RELATED ART

An acquisition of a stream of data points $\{t_i, s_i\}$ with $1 \leq i \leq z$, wherein z is an arbitrary number which refers to a number of the data points which are recorded within the stream of data points, wherein the stream of data points is consecutively acquired in a manner that a specific data point $(t_i, s_i)$ is acquired after a preceding data point $(t_{i-1}, s_{i-1})$, is a well-known problem which occurs in all areas of science and technology which are related to recording a scientific or technical effect which produces a signal $s_i$ at a time $t_i$. Typical examples are physical and/or chemical and/or biologic and/or environmental experimental data which may be recorded in the course of a scientific experiment but also during the surveillance of environmental data or the monitoring any kind of body functions of a user, in particular a patient. Many other examples are conceivable.

It is further well-known in the field of data acquisition that the stream of data points not always only comprises a valid value for a signal $s_i$ at a time $t_i$. In practice, the stream of data points may further comprise an invalid value for the signal $s_i$ at a time $t_i$, or, alternatively, a signal $s_i$ which is expected to be recorded at the specific time $t_i$ but which may be missing. However, this situation which is known from practical experience is particularly unsatisfying in a situation when a measurement has been scheduled to provide real-time or nearly-real time information, for example when determining one or more body functions of a user, such as a patient who is under permanent surveillance in an intensive care unit. Particularly in a situation where the real-time or nearly real-time information is required to trigger any further devices and/or to make a decision, invalid or missing values may seriously influence the results of the recording of the data points, in some situations even in an unintentional direction.

As an example, William L. Clarke, and Eric Renard, "Clinical Requirements for Closed-Loop Control Systems", Journal of Diabetes Science and Technology 6, No. 2, (2012) 444-452, refer to a closed-loop therapy system for type 1 diabetes mellitus patient use. Hereby, measures of glycemic variability are described and the recording of blood glucose levels as percentages within, above, and below a target range are suggested as reasonable alternatives to sophisticated statistical analyses. Therefore, detection methods are needed to warn both the system and the patient about altered insulin delivery, including internal pressure and flow alarms. Glucose monitor sensor accuracy is another requirement; it includes the definition of conditions that lead to capillary glucose measurement, eventually followed by sensor recalibration or replacement. The crucial clinical requirement will be a thorough definition of the situations when the patient needs to move from the closed-loop therapy system to manual management of insulin delivery, or inversely can switch back to the closed-loop therapy system after a requested interruption.

Particularly in order to suppress effects of random errors, while minimizing a loss or a distortion of underlying meaningful data, an extraction of information from the stream of data points has been achieved by employing a method which has been designated as "data smoothing". Hereby, an error reduction problem is considered for a sequence of related data values, particularly related to a time-series measurement of an observable, which is expected to follow a pattern which may not be known beforehand but which could be drafted in a two-dimensional representation and in which an error can be assumed to occur primarily in one of the two dimensions.

The majority of known error-reduction techniques involve the assumption that the recorded data points, at least locally, can be approximated or "fit" by a procedure, which often includes linear or higher-order polynomials and wherein usually a criterion of "least squares" with regard to deviations is employed. The use of the procedure particularly allows to minimize distortions by a piecewise polynomial approximation. Thereby, the set of data points used for the procedure is employed to slide along the entire data set. The more data points are used for the procedure, the better turns out the removal of random errors which is, however, achieved at cost of introducing a systematic error by an application of the procedure itself. A popular technique within this respect is a method which is designated as 'spline fit' which determines a set of cubic functions which connect data sub-regions. However, such polynomial regression based on this method may also lead to delays and distortions.

In a situation where a physical model has been found to be suitable to describe a recorded noise behavior, so-called "Kalman filters" have been developed to smooth the recorded data points. However, such filters are not applicable in a case where such a model is missing or inappropriate. As an example, when monitoring physiological data of a user in a real-life setting, it is not feasible to provide an appropriate physical model which could reasonably describe parameters like a glucose concentration behavior with respect to an insulin intake. Nevertheless, such a model which assumes a constant parameter, for example a glucose slope over a time or a second derivative of glucose over the time, have been proposed by B. Wayne Bequette, "Continuous Glucose Monitoring: Real-time Algorithms for Calibrating, Filtering, and Alarms," *Journal of Diabetes Science and Technology* 4, no. 2 (March 2010): 404-418, as well as by Andrea Facchinetti, Giovanni Sparacino, and Claudio Cobelli, "An Online Self-tunable Method to Denoise CGM Sensor Data," *IEEE Transactions on Bio-medical Engineering* 57, no. 3 (March 2010): 634-641, respectively. As a result, it is no surprise that delays and distortions are introduced into corresponding data sets. As an example, Giovanni Sparacino et al. suggest an algorithm in which model and filter parameters are found empirically from the recorded data points which need to be adapted to physiological changes as well as to variations between patients, sensors, or intrapatient variations over the time. Although this algorithm calculates the current best parameter from the data points in a given time interval in the past, there always remains a considerable risk that unforeseen physiological conditions or unusual sensor behavior leads to unexpected and possibly hazardous errors in the reporting of a set of smoothed data.

As an alternative, so-called "Wiener filters" have been proposed for the smoothing of glucose monitoring data, e.g. by K Rebrin et al., "Subcutaneous Glucose Predicts Plasma Glucose Independent of Insulin: Implications for Continuous Monitoring", The American Journal of Physiology 277, no. 3 Pt 1 (September 1999): E561-571, which have recently been employed in conjunction with a time-lag correction by D. Barry Keenan et al., "Interstitial Fluid Glucose Time-lag Correction for Real-time Continuous Glucose Monitoring", Biomedical Signal Processing and Control 8, no. 1 (January 2013): 81-89. Irrespective of their potential applicability for this purpose, Wiener filters suffer from the fact that they are based on complicated mathematical algorithms which impede their implementation.

Eugen and Ionela Iancu, "Predictive Blood Glucose Control Using Exponential Smoothing Method", Annals of the University of Craiova, vol. 8 (36), no. 2, p. 1-6, 2011, present the structure of a predictive algorithm adapted to remove erroneous values from a stream of patient data acquired by means of a continuous glucose monitoring system. For this purpose, single exponential smoothing employing a smoothing constant α is used for smoothing discrete time series, wherein a is a number selected from an interval 0<α<1.

Further, US 2008/0167841 A1 discloses a system and a method for processing as stream of data by using scaled exponential smoothing in order to maintain a histogram.

J. Haworth and Tao Cheng, "Non-parametric regression for space-time forecasting under missing data", Computers, Environment and Urban Systems, vol 36, no. 6, p. 530-550, 2012, deal with real-time spatio-temporal data sets for providing predictive information about spatio-temporal processes. Within this regard, they demonstrate that a presence of spatio-temporal autocorrelation in a time-space series of data improves respective forecasts. In particular, a non-parametric spatio-temporal kernel regression method is employed for predicting future unit journey time values of road links in central London under the assumption of sensor malfunction and compared with other kinds of non-parametric regression methods known to be effective for this purpose. D. E. Roark, "Reverse Smoothing: a model-free data smoothing algorithm", Biophysical Chemistry 108 (2004) 121-126, proposes a method called by him "reverse smoothing" which has the ability to significantly reduce or eliminate the time-lag effect while maintaining a benefit from the noise-reduction of exponential smoothing, a well-known technique which is, for example, described in C. Holt, "Forecasting seasonals and trends by exponentially weighted moving averages", International Journal of Forecasting 20 (2004) 5-10; reprint of an original article from 1957. According to Roark, this method appears appropriate in a situation where the set of data points is expected to exhibit a smooth behavior. Also, a sufficient number of data points is further necessary in order to locally characterize a slope. As a typical example Roark employs his method to 80 data points. Moreover, in a region where the slope rapidly changes, a higher density of data points is required. Roark employs exponential smoothing, however, not on the original data but on the estimated first derivatives of the original data. In order to achieve a good smoothing, three consecutive performances, which are called "passes", of exponential smoothing are performed on the respective set of slopes. Hereby, the first pass is a so-called "forward pass" from the second point to the last point within the set of data points whereas the second pass is a so-called "reverse pass" from the next to last point to the first point within the set of data points. A third forward pass concludes the smoothing process. According to Roark, the smoothing procedure which acts on the first derivatives of the set of data points more effectively removes random fluctuation with less introduction of a distortion to the underlying data. As will be explained below in further detail, it has, however, been found that this method as proposed by Roark, faces severe problems when a large number of missing values is comprised within the stream of data points, in which case intolerable errors are introduced into the smoothing process. Moreover, the algorithm was designed to be used on complete data sets, not on a stream of data. Because of the reverse pass, output can only be generated by the original Roark procedure after the acquisition of data has been completed.

Problem to be Solved

It is therefore an objective of the present invention to overcome the shortcomings and disadvantages of known methods and apparatus for determining at least one smoothed data point within a stream of data points. In particular, it is intended to propose a respective method which could provide a good degree of smoothing without introducing any lag time and with minimal distortions, and is even capable of reporting derivatives at the same time. In addition, such a method should be computationally simple and should be able to employ fixed parameters without any requirement to adjust such parameters to individual users, sensors, or day-to-day variations. In particular, this method should allow for a real-time or a nearly real-time reporting despite the fact that the recorded data are not required to be equally or nearly equally spaced.

It is a further objective of the present invention to provide an apparatus which allows minimizing the power consumption as well as an exposure of a sensor undisturbed by the measurement means, such as an impinging the sensor with radiation.

It is a further objective of the present invention to provide a use for the apparatus in situations for which the apparatus is particularly suited.

It is a further objective of the present invention to provide a computer program which should include computer-executable instructions for performing the method according to the present invention when the program is executed on a computer or a computer network.

It is a further objective of the present invention to provide a data carrier which should have a data structure stored thereon, which, after loading into a computer or a computer network, is capable of executing the method according to the present invention.

SUMMARY OF THE INVENTION

This problem is solved by a method, by an apparatus and by a use of the apparatus for determining at least one smoothed data point within a stream of data points as well as by a computer program and by a data carrier with the features of the independent claims. Preferred embodiments, which might be realized in an isolated fashion or in any arbitrary combination, are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context as well as to a situation in which one or more further features are present. As an example, the expressions "A has B", "A comprises B" and "A includes B" may both refer to a situation in which, besides B, no other element is present in A (i.e. a situation in which a solely and exclusively consists of B) and to a situation in which, besides B, one or more further elements are present in entity A, such as element C, elements C and D or even further elements.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, the present invention refers to a method for determining at least one smoothed data point $(t_k, s_k)$ within a stream of data points $\{t_i, s_i\}$, wherein $1 \le i \le z$ refers to the i-th data point $(t_i, s_i)$ in the stream of data points $\{t_i, s_i\}$, wherein $1 \le k < z$ refers to the k-th smoothed data point $(t_k, s_k)$, wherein the k-th smoothed data point $(t_k, s_k)$ will be determined by the method according to the present invention within the stream of data points $\{t_i, s_i\}$, wherein i, z, and k are integers. As further used herein, the stream of data points is considered as a set of z data points, wherein the data points are acquired according to a chronological sequence in a manner that the acquisition of a specific data point $(t_i, s_i)$ is performed after a time interval $\Delta t$ after which the acquisition of a preceding data point $(t_{i-1}, s_{i-1})$ has been performed. Hereby, the number z constitutes an arbitrary numerical value which refers to a number of data points recorded within a specific stream of data points. As an example, the number z may be a low number as 1, 2, 3 . . . etc. but, in practice, rather a large number of several tenths, hundreds, thousands, or even more data points. With respect to the present invention, it is particularly emphasized that the absolute value of the number z is of little importance since the respective method is particularly intended for a real-time or a nearly real-time reporting of data points and may be already employed while the stream of data points is still under further recording. However, other manners of employing the present method are conceivable, for example that a smoothing process only commences after data acquisition has been concluded.

The preferred feature of the present invention of being able to already starting the smoothing process while the acquisition of the stream of data points is still performed is in particular contrast to the state of the art. For example, the method for determining the smoothed data points as described by Roark, requires that such a method cannot start before the whole set of data points has been collected. In contradiction to the state of the art, it has, moreover, been found that the algorithm according to the present invention is able to smooth even short sets of data points, i.e. a set of data points which comprises a comparatively low number z of data points, particularly in the range below 20, even below 10. Consequently, the method according to the present invention allows already to determine at least one smoothed data point within an incoming stream of data points, irrespective of the fact whether all z data points within the stream have already been recorded or not. In an alternative fashion, however, the present method is still applicable in a situation where all z data points within a stream of data points have already been collected.

Similar to methods known from the state of the art, each data point $(t_i, s_i)$ in the stream of data points $\{t_i, s_i\}$ may comprise a valid value for a signal $s_i$ at a time $t_i$. Herein, the valid value for the signal $s_i$ is a value which is recorded at a time $t_1$, wherein "recording a signal $s_i$ at a time $t_i$" particularly means acquiring any physical, chemical, biological, environmental, and/or technical data by means of any technical set-up, whereby a second set of data is recorded, wherein a value within the second set designates a time $t_i$ which is associated with the signal $s_i$. In particular, the respective value in the second set delivers the actual time $t_i$ at which or about which the related signal $s_i$ was recorded and/or is related to in any other way. By way of example, the signal $s_i$ may be an amplitude or another physical quantity in relationship to a voltage or to a current and/or to an electronically implemented equivalent thereof whereas the value for the time $t_i$ related with the signal $s_i$ may be the value in the second set of data which may be generated by any kind of clock and/or watch and/or timer and/or an electronically implemented equivalent thereof. More specific and non-limiting examples may include a signal which may be related to a concentration of a substance in a volume, for example to a glucose concentration in a body fluid, preferably in an interstitial fluid. Other examples may include at least one cardiac function of a user, for example a pulse and/or a blood pressure and/or an electronic signal related to an electrocardiographic (ECG) signal of a user, such as a patient. A further example refers to a signal being recorded by an application of electroencephalography (EEG) which is adapted to record the electrical activity along a scalp of a user.

With respect to the present method, the value for the signal $s_i$ at a time $t_i$ is considered as being "a valid value" as long as the recorded value $s_i$ constitutes a meaningful event within the design of the technical set-up which is configured to deliver the stream of data points $\{t_i, s_i\}$. Hereby, a meaningful event may occur when the value for the signal as delivered by the technical set-up may be within an expected range of possible values and may, thus, be designated as "valid" by a procedure which has been implemented within the technical set-up and/or within any other device which may receive a stream of data points from the technical set-up. The technical set-up usually includes a sensor which is adapted to record a series of signals $s_i$ and to simultaneously record a second data point which is related to a time $t_i$. Alternatively, the sensor may be configured to only record a series of signals $S_i$ while the second series of data points which are related to the time $t_i$ are recorded by means of a separate device, preferably a clock and/or a watch and/or a timer, which is located outside the technical set-up adapted for recording a series of signals $s_i$. In addition, such a sensor may already include a simple or a more elaborate evaluation unit which may be configured to perform at least a basic evaluation procedure, which may allow to distinguish between a valid value and an invalid value. As further used herein, an "invalid value" is a value for the signal $s_i$ which, although having been recorded at a time $t_i$, does not fulfill the above-mentioned criteria for a meaningful value of the signal $s_i$ and can, thus, be considered as erroneous. It is emphasized here that for the method according to the present invention, it is not of any relevance at which point a decision, whether a recorded value for the signal $s_i$ is determined to be a "valid value" or to be an "invalid value" is actually taken. The method is applicable in the same manner irrespective of the fact whether such a distinction is already performed on the level of the technical set-up and/or in a specific stage during the performance of the method according to the present invention as will be specified later and/or at any intermediate stage, which may be performed, for example, in a separate device which is adapted for executing this kind of discrimination. In addition, it does not make any difference for the actual performance of the method according to the present invention in which form an invalid value is delivered, for example whether an invalid value still comprises an actual number such as a voltage and/or a current value or whether it has already been tagged with a sign which indicates that this specific value is designated as an invalid value.

In addition and in further contrast to the state of the art, the present method is further appropriate to deal with a missing value for the signal $s_i$ at a time $t_i$. As further used herein, the "missing value" comprises an expected time $t_i$ at which time no signal $s_i$ has been provided by the technical set-up as a part of the input stream of data points $\{t_i, s_i\}$. This particular feature is well-known from real-time or nearly real-time information where a technical set-up is usually expected to deliver a signal $s_i$ at least once within a specified time interval. As already described above, signals as acquired by the technical set-up during the real-time or nearly real-time measurement, are often used as a basis for a further decision to be taken on the basis of the specific recorded value. As an example, a further treatment of a patient will depend on the actual value of the signal $s_i$, which, for example, delivers a blood glucose level, which has been recorded most recently. Usually, such a measurement series is arranged in a manner that the time interval between two consecutively acquired signals is chosen to be in relationship with a known or an expected variation time of the actual signal. For example, in an intensive care unit and/or a closed-loop therapy system it may be not sufficient to simply use the actual value of the most recent signal $s_i$ as acquired by the measurement series, particularly in a case where a long time has passed since the time $t_i$ at which this specific signal has been recorded. As will be described below, the method according to the present invention, still allows to determining at least one smoothed data point in such a situation when a value for the signal $s_i$ is missing at a time $t_i$.

The method according to the present invention comprises the steps a) to g). These steps are preferably performed in the given order, starting with step a). However, one or more steps may be preformed repeatedly, dependent or independent whether other steps are equally repeated.

According to step a), a set of data points is provided. This set of data points may preferably comprise the stream of data points $\{t_i, s_i\}$ which has been acquired in a manner as described above, i.e. that two adjacent data points have been consecutively recorded with respect to their order. However, the present method is still applicable in a situation where a specific set of data points is selected from the acquired stream of data points $\{t_i, s_i\}$ and providing this specific set of data points with step a). Furthermore, it may also be favorable in a specific case to provide a specific data set with step a) which is selected from a set of already smoothed data points $\{t_k, s_k\}$, particularly for further smoothing, wherein the specific set may be selected by a procedure which will be described later in more detail.

The smoothing process for the data point $(t_i, s_k)$ is commenced during the following step b). Therefore, for each smoothed data point $(t_k, s_k)$, a smoothing set is created. This kind of procedure is in particular contrast to the state of the art, as e.g. described in Roark et al., wherein the complete data set is used for the purpose of smoothing after its complete acquisition. Whereas this method known from the state of the art requires that the whole set of data points has been collected prior to its commencing, here the smoothing set may also be selected according to step a) directly from the stream of data points $\{t_i, s_i\}$. Consequently, the method according to the present invention may not only be able to deal with continuously acquired data but may also provide means for continuously monitoring the acquired set of data points.

For this purpose, the smoothing set comprises a subset of data points $\{t_\ell, S_\ell\}$, in particular a genuine subset of the set of data points $\{t_\ell, S_\ell\}$, wherein the subset of data points has been acquired from the set of data points as provided during the preceding step a) by selecting data points $(t_\ell, S_\ell)$ which fulfill Equation 1:

$$(k+\text{offset}-\text{smoothing window}+1) < \ell < (k+\text{offset}) \qquad (1)$$

In Equation 1, offset>0 comprises a numerical value which constitutes an offset number. As further used herein, the "offset number" delivers an offset which comprises number of data points $(t_i, s_i)$ with $t_i > t_k$ which have been acquired ahead of the specific data point $(t_k, s_k)$ for which the smoothing process according to the invention is currently performed. The offset data points, thus, comprise a number of data points which have been recorded before the commencing of the smoothing process for the specific data point $(t_k, s_k)$ which is under current smoothing in the process as described in step b). It is emphasized here that the offset data points only include such data points which comprise a valid value as defined above. In a preferred embodiment, an additional condition may be verified whether at least one data point, or more preferably, whether all offset data points may have a valid value after having removed a number of data points from the smoothing set during the verifying step. If the additional condition may not be fulfilled, no value for the smoothed data point $(t_k, s_k)$ may be determined and no smoothed data point $(t_k, s_k)$ or an error flag may be returned. As further used herein, the smoothing window as used in Equation 1 is defined as a numerical value which delivers a length of the smoothing set. Preferred values for the numerical values offset and smoothing window will be given below.

Prior to the next step c), a criterion is applied to a data point in order to decide whether this data point is retained or discarded with respect to the further steps c) to g) of the method according to the invention. Hereby, the criterion may comprise a verifying step, according to which it is decided whether the data point may comprise a valid value, or an invalid value, or a missing value according to the above definitions. In particular, only the data point which comprises a valid value may be retained for further processing, whereas the data point which comprises one of an invalid value or a missing value may be discarded and, thus, not used in the further processing according to the method.

The verifying step may be applied prior to step b) for each data point in the set of data points as provided according to the preceding step a). Alternatively or in addition, the verifying step may also be applied after step b) for each already selected data point as provided in the smoothing set according to step b). It is emphasized, however, that, irrespective of the details of the verifying step and/or of the moment when the verifying step is applied, the verifying step is particularly to be performed prior to step c) in order to be able to define a gap length, which will be further described below.

According to step c) of the present method, for each smoothed data point $(t_k, s_k)$ it is verified whether a first condition is fulfilled. Hereby, the "first condition" requires that in each pair of two adjacent data points $\{(t_\ell{}_{-1}, t_\ell{}_{-1}), (S_\ell, S_\ell)\}$ within the smoothing set the condition according to Equation 2:

$$(t_\ell - t_\ell{}_{-1}) \leq \text{gap length} \tag{2}$$

is actually fulfilled. As further used herein, the numerical value "gap length" defines a maximum time difference which is admitted between the two adjacent data points within the smoothing set. As described above, gaps have been introduced by employing a criterion in a verifying step by which, consequently, a number of data points may be discarded from the set of data points which is used as an input to step c). This procedure reflects the actual situation in a real-time or a nearly real-time measurement wherein a gap may occur in which only invalid values may be acquired and/or values may be missing. Further according to step c), the data points $(t_\ell, S_\ell)$ with $\ell < \ell_0$ are removed from the smoothing set in case the first condition according to Equation 2 is not fulfilled for a certain $\ell_0$. Such a situation may particularly happen when a large gap occurs within the stream of data points during the measurement series. In this case, data points which are acquired earlier with respect to the gap length are discarded as trailing data.

According to step d) of the present method, it is verified whether a second condition is fulfilled. Hereby, the "second condition" requires that a numerical value n equals at least a numerical value minimal window. Whereas the numerical value n is defined to equal the number of data points $(t_i, s_i)$ which remain in the smoothing set after the preceding step c), the numerical value "minimal window" delivers the number of data points $(t_\ell, S_\ell)$ which are required to remain in the smoothing set after the preceding step c). The second condition is intended to examine whether the remaining number n of data points in the smoothing set $\{t_\ell, S_\ell\}$ equals at least the predefined value of minimal window. Therefore, the second condition ensures that the smoothing set which is required for the subsequent steps e) to g) comprises a sufficient number of data points. Consequently, in case the second condition is not fulfilled, no value for the smoothed data point $(t_k, s_k)$ is determined. In such a case, the present method may either deliver no smoothed data point or, alternatively, return an error flag which indicates that no smoothed data point could be determined from the data points which were provided during step a) and not discarded in the subsequent verifying step.

However, in case the second condition is fulfilled, the method according to the present invention is continued with the subsequent step e). According to step e), for each smoothed data point $(t_k, s_k)$ a slope set $\{t_\ell, S_\ell'\}$ is calculated comprising one data point $(t_\ell, S_\ell')$ for each data point $(t_\ell, S_\ell)$ in the smoothing set with $1 < \ell < n$. As further used herein, a "slope" delivers a value for an incline and/or a decline which a virtual line which is placed through a set of data points $\{t_m, s_m\}$ will experience at a specific data point $(t_\ell, S_\ell)$. Consequently, the slope set $\{t_\ell, S_\ell'\}$ is defined as the derivative or gradient of the set of data points $\{t_\ell, S_\ell\}$.

In a preferred embodiment, step e) may comprise the following sub-steps e1) to e3), which may be preferably performed in the given order.

According to sub-step e1), a numerical value "SlopeRange" may be defined as a number of data points which may be employed to calculate the slope $S_\ell'$ at each data point $(t_\ell, S_\ell)$ in the smoothing set. According to sub-step e2), the further processing may depend on the fact whether the numerical value SlopeRange may be an odd number or an even number. In case the numerical value SlopeRange is an odd number, a number of (SlopeRange–1)/2 data points before and a number of (SlopeRange–1)/2 data points after each data point $(t_\ell, S_\ell)$ may be selected as a differentiation set $\{t_m, s_m\}$ for the respective data point. Within this regard, it may be required to consider whether the selected data points exist, i.e. whether a particular data point $(t_\ell, S_\ell)$ is far enough from a beginning or from an end of the smoothing set, since only such data points may be employed in the following sub-step. However, if a data point $(t_m, s_m)$ is missing because $(t_\ell, S_\ell)$ is too near to the beginning or to the end of the smoothing set and $\ell$ is smaller than (SlopeRange–1)/2+1 or larger than n–(SlopeRange–1)/2, this specific data point is ignored and the differentiation set $\{t_m, S_m\}$ consists only of those selected data points which do exist. On the other hand, if the numerical value SlopeRange may be an even number, a number of (SlopeRange/2) data points before and a number of (SlopeRange/2–1) data points after each data point $(t_k, s_k)$ may be selected as the slope set for the respective data point. Here, also the same requirements with regard to the existence of the selected data points are applicable.

According to the subsequent sub-step e3), the slope $S_\ell'$ for each of the data points $(t_\ell, S_\ell)$ in the smoothing set may be calculated according to Equation 3:

$$s'_\ell = \frac{d\sum_{m=1}^{d} t_m s_m - \sum_{m=1}^{d} t_m \sum_{m=1}^{d} s_m}{d\sum_{m=1}^{d} t_m^2 - \sum_{m=1}^{d} t_m \sum_{m=1}^{d} t_m} \tag{3}$$

Hereby it is mentioned that in Equation 3, the respective sums $\Sigma$ may be calculated over the data points in the differentiation set $\{t_m, s_m\}$ with d either being equal to SlopeRange or being smaller than SlopeRange in a case where data points did not exist at the ends of the smoothing set, and the calculation is performed for each point in the smoothing set, $1 \leq \ell \leq n$, whereby the slope set $\{t_\ell, S_\ell\}$ is created from the resulting points $(t_\ell, S_\ell)$.

After the slope set has been acquired during step e), for each smoothed data point $(t_k, s_k)$ at least one exponential smoothing may be applied to the slope set $\{t_\ell, S_\ell\}$ as provided by the previous step e).

In a particularly preferred embodiment, step f) may comprise the following sub-steps f1) to f3) by which the at least once modified slope set $\{t_\ell, S_\ell'^*\}$ may be determined and which may be preferably applied in the mentioned order. It is mentioned that this particular embodiment follows closely the procedure as proposed by Roark described above, however, the specific weights which may be used for performing steps f1) to f3) may be adapted to the specific requirements of the processing of real-time or nearly real-time information.

According to sub-step f1), a first forward exponential smoothing may be applied to the slope set $\{t_\ell, \ell'\}$ as acquired in the preceding step e) in an ascending order 1, 2, ..., n−1, n. Hereby, the following relationship according to Equation 4 may be applied:

$$s_1'^* = s_1' \text{ and}$$

$$\ell'^* = W_{f1} \cdot \ell' + (1-W_{f1}) \cdot \ell_{-1}' \text{ for } 1 < \ell \le n, \quad (4)$$

wherein $W_{f1}$ is a first weight which is adapted for the first forward exponential smoothing.

According to sub-step f2), a reverse exponential smoothing may be applied to the slope set $\{t_\ell, \ell'^*\}$, which has already been modified in the preceding sub-step f1), in a descending order n, n−1, ..., 2, 1. Hereby, the relationship according to Equation 5 may be applied:

$$s_n'^{**} = s_n'^* \text{ and}$$

$$\ell'^{**} = W_r \cdot \ell'^* + (1-W_r) \cdot \ell_{+1}'^* \text{ for } 1 \le \ell < n \quad (5)$$

wherein $W_r$ is a second weight which is adapted for the reverse exponential smoothing.

According to sub-step f3), a second forward exponential forward smoothing may be applied to the slope set $\{t_\ell, \ell'^{**}\}$, which has been further modified in the preceding sub-step f2), in an ascending order 1, 2, ..., n−1, n. Hereby, the smoothing may be performed according to Equation 6:

$$s_1'^{*} = s_1'^{} \text{ and}$$

$$\ell'^{*} = W_{f2} \cdot \ell'^{} + (1-W_{f2}) \cdot \ell_{-1}'^{**} \text{ for } 1 < \ell \le n, \quad (6)$$

wherein $W_{f2}$ is a third weight adapted for the second forward exponential smoothing.

According to step g) of the method according to the present invention, the last modified slope set as determined in the preceding step f), which is here described by $\{t_\ell, \ell'^{***}\}$ is integrated for each smoothed data point $(t_k, s_k)$. By this procedure, the designated value for the smoothed data point $(t_k, s_k)$ is finally determined and subsequently returned.

In a preferred embodiment, step g) may comprise the following sub-steps g1) to g5), which may be preferably performed in the given order.

According to sub-step g1), an average "orig mean" of the values $1 \le \ell \le n$ within the smoothing set as acquired prior to step e) may be calculated. For this purpose, a central value for smoothed data points within the smoothing set may be acquired, particularly by dividing the sum of the values of the smoothed data points within the smoothing set by the number of the smoothed data points within the smoothing set.

Then, according to sub-step g2), the last modified slope set $\{t_\ell, S\ell'^{***}\}$ may be numerically integrated according to Equation 7:

$$\text{integral}_1 = 0 \text{ and}$$

$$\text{integral}_\ell = \text{integral}_{\ell-1} + [(1-w_i) \cdot S\ell'^{*} + w_i \cdot S\ell_{-1}'^{*}] \cdot [S\ell - S\ell_{-1}] \text{ for } 1 < \ell < n, \quad (7)$$

wherein $w_i$ is a fourth weight which is adapted for integrating.

By this sub-step g2), an integrated set is acquired for which, according to sub-step g3), an average "new mean" of the values of integral$_i$, with $1 < i < n$ may be calculated. For this purpose, a central value for integrals within the integral set may be acquired, particularly by dividing the sum of the values of the integrals within the integral set by the number of the integrals within the integral set.

According to the next sub-step g4), an integration constant "int const" may be calculated by applying Equation 8:

$$\text{int const} = \text{orig mean} - \text{new mean}; \quad (8)$$

According to sub-step g5), the smoothed value of $s_k$ may be finally calculated by application of Equation 9:

$$s_k = \text{integral}_k + \text{int const} \quad (9)$$

By this procedure the value for the at least one smoothed data point $(t_k, s_k)$ with k=n−offset may be determined and returned.

Consequently, a smoothed data point $(t_k, s_k)$ within a stream of data points $\{t_i, s_i\}$ has been determined by the method according to the present invention. However, in a further step the method may be continued for a next smoothed data point $(t_{k+1}, s_{k+1})$ by consecutively performing steps b) to g) for the next smoothed data point $(t_{k-1}, s_{k+1})$. By this way, the method according to the present invention may be performed as long as a data point may be required. Alternatively, any arbitrary data point as taken from the stream of data points may be employed for calculating at least one further smoothed value.

In a particularly preferred embodiment, at least one triple data point $(t_k, s_k, s_k')$ is returned. Hereby, the triple data point $(t_k, s_k, s_k')$ additionally includes a value $s_k'$ for the derivative of the smoothed value $s_k$. As presented above, the present method easily allows to return such a triple data point which delivers a derivative from a time series measurement which is often required for further evaluation purposes.

In a particularly preferred embodiment, any or all of the numerical values with respect to the offset, the smoothing window, the gap length, the minimal window, the SlopeRange, the first weight $W_{f1}$ for first forward exponential smoothing, the second weight $W_r$ for the reverse exponential smoothing, the third weight $W_{f2}$ for the second forward exponential smoothing, and/or the fourth weight $w_i$ for integrating may be chosen from preferred intervals, more preferred intervals, if applicable, and/or most preferred values as presented in Table 1. However, it is emphasized here that other values for the numerical values as given in Table 1 may be selected for specific purposes with regard to the application of the method according to the invention. On the other hand, it could be experimentally demonstrated as presented below that a performance of the method with values taken from the values and/or ranges as given in Table 1 for the respective numerical values already provide a good smoothing, particularly on short time scales.

TABLE 1

| Numerical value | Preferred interval | More preferred interval | Most preferred value |
| --- | --- | --- | --- |
| Offset | [1, 4] | | 2 |
| smoothing window | [7, 40] | [15, 25] | 20 |
| gap length | [5 Δt, 30 Δt] | [5 Δt, 15 Δt] | 6 Δt |
| minimal window | [5, 20] | [5, 10] | 5 |
| SlopeRange | [3, 6] | | 3 |
| first weight $W_{f1}$ for first forward exponential smoothing | [0.3, 0.6] | | 0.5 |
| second weight $W_r$ for reverse exponential smoothing | [0.2, 0.5] | | 0.33 |
| third weight $W_{f2}$ for second forward exponential smoothing | [0.3, 0.6] | | 0.5 |
| fourth weight $w_i$ for integrating | [0.25, 0.75] | | 0.33 |

In a further preferred embodiment, the specific set as provided in step a) may be selected by taking every p-th item, where p is a numerical value which may be preferably chosen from an interval [2, 6], whereby 3 is the most preferred value. By this procedure, only every p-th data point may be retained in the specific set whereas the other data points may be discarded.

This procedure may be preferably employed in the following way: First, the original stream of data points is used as the set of data points according to step a), wherein a first performance of the presented method with the steps b) to g) may be commenced. Alternatively, from the original stream of data points a reduced set of data points can already be produced and used as the specific set according to step a), wherein a first performance of the presented method with the steps b) to g) may be commenced. Thereafter, the stream of smoothed data points or a selected number of data points taken from the stream of smoothed data points can be used as a further input for the set of data points according to step a), wherein, subsequently, the further steps b) to g) are applied in a second performance. Hereby, the parameters, as for example presented in table 1, may be chosen to be the same for the first performance and for the second performance or may be chosen to be different with respect to the two performances. Moreover, other numerical values compared to those which are comprised in Table 1 may be applied.

Alternatively or in addition, the specific set as provided in step a) is selected by providing one of p subsets, wherein the q-th subset comprises a number of items $(t_i, s_i)$ with i=q, p+q, 2p+q, . . . , with q=1, 2, . . . and with q<p, as long as each of the item comprises a valid value. In a specific embodiment, the p subsets may be merged after smoothing, preferably after applying calculating means on corresponding items within the p subsets. By way of example, the p subsets may be merged for example without further processing, which would result in the same number of data points compared to the input data set. Another example may be merging the p smoothed data sets by further applying calculating means, such as arithmetic means, medians and/or other procedures, on the times and/or on the signals, which would result in a reduced number of data points compared to the original data set. A further example may be the application of calculating means on the times and/or on the signals with respect to a merger of the n smoothed data sets in a sliding manner, whereby also the same number of data points as in the original data set would result. By a "sliding manner" a procedure is defined in which window is subsequently moved over each of the data points to each of which the calculating means are applied with regard to their respective neighbors. In a further example which may, in addition, also applied to the other examples, data points may be eliminated according to a specific criterion before the calculating means may be applied. This procedure may be particularly useful for reporting data triples $(t_k, s_k, s_k')$, whereby the process of merging and calculating means is also applied to the corresponding slopes $s_i'$.

According to the present invention, the data point $(t_i, s_i)$ is preferably acquired after the specific time interval $\Delta t=(t_i-t_{i-1})$ after the acquisition of the preceding data point $(t_{i-1}, s_{i-1})$. This definition reflects a situation in which in a real-time or a nearly real-time measurement series the data points may be recorded regularly, each after a time interval $\Delta t$. However, it may be preferable, particularly in the case when the preceding data point $(t_{i-1}, s_{i-1})$ may comprise an invalid value or comprises a missing value, that the time interval $\Delta t$ may not be a constant value, which describes for example the case when the specific data point $(t_i, s_i)$ is acquired at a point of time $t_i$ which is prior to the end of the time interval $\Delta t$ for one or more preceding consecutive pairs of data points. This procedure may be particularly performed by a standard sampling rate with the time interval $\Delta t$, wherein, immediately after receiving a data point, a verifying step may be performed which may return the information whether the reading delivered an actual point at all and whether the received data point is valid. In case a missing data point or an invalid data point occurs, a second reading may be performed earlier, preferably as fast as possible, in particular considerably earlier than given by the sampling interval.

Within this regard, the specific set may be selected by retaining items at data points with $t_0$, $t_0+r\cdot\Delta t$, $t_0+2r\cdot\Delta t$, . . . with 0<r, r being an integer, or, alternatively, an adjacent item, in particular wherein the adjacent item is a distance of $\pm\Delta t$ or at a distance of $\pm2\cdot\Delta t$ from the data point $(t_i, s_i)$ which comprises an invalid value or a missing value. This procedure is particularly applicable in a case where large gaps within the stream of data points may very likely occur.

In a particularly preferred embodiment, the stream of data points $\{t_i, s_i\}$ may comprise a measurement series which may consecutively be recorded by a sensor. Hereby, the sensor may be adapted for recording the signal $s_i$ at a time $t_i$, wherein the signal $s_i$ may be particularly related to a concentration of a substance in a volume. Consequently, the sensor may be selected to preferably be an optical sensor, in particularly a fluorescence sensor, which may be especially adapted for determining a glucose concentration in a body fluid, such as an interstitial fluid. However, other embodiments in which the method according to the present invention would work in a comparable manner are conceivable.

A further aspect of the present invention refers to an apparatus for determining at least one smoothed data point $(t_k, s_k)$ within a stream of data points $\{t_i, s_i\}$ with 1≤i≤z, k<z, where i, z, and k are integers. According to the present invention, the apparatus comprises an instruction device which is adapted for instructing a sensor to record a series of signals $s_i$ at a time $t_i$ and to deliver a stream of data points $\{t_i, s_i\}$ to the apparatus, wherein at least some of the data points $(t_i, s_i)$ within the stream of data points $\{t_i, s_i\}$ comprise a valid value for the signal $s_i$ at a time $t_i$. Hereby, the sensor may be a constituent part of the apparatus, however, in a more preferred embodiment the sensor is constructed as a separate arbitrary body which is located outside the housing of the apparatus. Within this regard, each and every sensor which has been described above may be applicable within the apparatus.

The apparatus further comprises a receiving and storing device, which is configured to receiving and subsequently storing the stream of data points $\{t_i,s_i\}$. For such a device any known memory for a storing of information in the form of data points may be employed.

The apparatus further comprises a calculating device which is adapted to determining at least one smoothed data point $(t_k, s_k)$ within the stream of data points $\{t_i, s_i\}$ with 1<i<z. Therefore, any computer and/or microcomputer and/or hardware implemented device may be employed for performing this purpose.

In a particularly preferred embodiment, the apparatus may be separated into two mechanical parts, whereby the instruction device may be mechanically coupled to the sensor, and, by way of example, may be worn on or near the human body where the sensor may be applied, and whereby the instruction device may comprise a wireless sending function, and whereby the receiving and storing device and the calculating device may be mechanically coupled together, and by way of example may be carried by the user or can be left under supervision of a nursing staff.

Hereby, the instruction device, the receiving and storing device, and the calculating device, which together form at least a part of the apparatus are configured to perform any steps according to the method for determining at least one smoothed data point within a stream of data points as described above. Within this regard, it is explicitly emphasized that all and any specific embodiments which have been described with respect to the method, may mutatis mutandis also be applicable to the apparatus.

In a preferred embodiment, the apparatus may be an analytical device for determining at least one body function of a user, wherein the apparatus may further comprise at least one sensor for recording at least one body function of the user, such as a patient. Hereby, the at least one sensor may be selected from the group consisting of: a sensor for measuring an analyte concentration of at least one analyte in a body tissue or a body fluid of the user; a cardiac sensor for determining at least one cardiac function of the user; a pulse sensor; a blood pressure sensor; an ECG; an EEG. However, other sensors which are particularly adapted to record physical and/or chemical and/or environmental parameters may also be applicable.

A further aspect of the present invention relates to a use of the apparatus for a purpose, which is particularly selected from the group consisting of: measuring an analyte concentration of at least one analyte in a body tissue or a body fluid of the user; determining at least one cardiac function of the user; determining a pulse of the user; determining a blood pressure of the user; recording an ECG; recording an EEG. However, the apparatus may also be used for other purposes, in particular for measuring a physical and/or chemical and/or biological and/or environmental value which may be accessible by the specifically selected sensor. Regardless of the mentioned applications, the present method and apparatus may particularly be used for an in-depth analysis of a stream of data points which have been obtained for example in a clinical trial as well as for real-time or nearly real-time data acquisition in a commercial medical device.

The invention further discloses and proposes a computer program including computer-executable instructions for performing the method according to the present invention in one or more of the embodiments enclosed herein when the program is executed on a computer or computer network. Specifically, the computer program may be stored on a computer-readable data carrier. Thus, specifically, one, more than one or even all of method steps a) to d) as indicated above may be performed by using a computer or a computer network, preferably by using a computer program.

The invention further discloses and proposes a computer program product having program code means, in order to perform the method according to the present invention in one or more of the embodiments enclosed herein when the program is executed on a computer or computer network. Specifically, the program code means may be stored on a computer-readable data carrier.

Further, the invention discloses and proposes a data carrier having a data structure stored thereon, wherein the data structure, after loading into a computer or computer network, such as into a working memory or main memory of the computer or computer network, may execute the method according to one or more of the embodiments disclosed herein. As further used herein, a computer comprises any device which may be capable of storing data and/or performing calculating steps and/or instructing steps.

By way of example, this definition not only includes workstations and notebooks but also ASICs (application specific integrated circuits) and FPGA (field-programmable gate arrays).

The invention further proposes and discloses a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the invention proposes and discloses a modulated data signal which contains instructions readable by a computer system or computer network, for performing the method according to one or more of the embodiments disclosed herein.

Preferably, referring to the computer-implemented aspects of the invention, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

The present invention comprises a number of advantages over the start of the art. First, the invention applies a sliding subset of the data point which is called smoothing set. The smoothing set which mostly refers to the past, may report only a single output value which results from a performance of the smoothing procedure according to the present method. The single output value may be particularly reported from the vicinity of the later end of the smoothing set, and the process may be repeated for the next output value with a new smoothing set. By applying this kind of arrangement, it may be feasible to report any measurement values in real-time or in nearly real-time while a high degree of smoothing may be still obtained. This advantageous effect is one of the main achievements of the present invention and constitutes one of the major differences to the state of the art.

Secondly, the estimation of the slopes may be performed in a manner that the end points of an interval which may be defined by the SlopeRange may be correctly taken into account. As will be shown in more detail below, the method according to the present invention delivers meaningful values with the data, thus avoiding distortions towards the end of the data set. Since Roark has always performed the smoothing according to his method on entire data sets, he was not particularly interested in values near the endpoints. However, for providing a real-time or a nearly real-time output it preferred that the values near the end points of the smoothing set may be as good as possible.

Third, the method according to the present invention correctly deals with gaps, particularly with large gaps, which may likely occur in real-time or in nearly real-time measurements within a stream of data points. As will be presented later, intolerable errors which are produced by the algorithm of Roark are avoided by the method according to the present invention. In particular, the mentioned sub-steps of restricting the size of the gaps together with an application of a smoothing subset circumvent these problems.

Fourth, a major advantage of the present invention may be the application of preprocessing of the data. It has been found that the method according to the present invention turns out to be good at smoothing out noise on a time scale of 1 to 5 sampling intervals but, on the other hand, adjusts its output to slower variations. If such variations may be smoothed, the spacing of the data may be preferably increased. It has been found that the preprocessing may deliver better results in combination with reverse smoothing. Combining two performances of a standard exponential smoothing with an intermediate data reduction results in a satisfactory smoothing but introduces large lag times which may be comparable to a sliding average which looks back over 30 data points.

Fifth, a further advantage feature of the present invention is based on the fact that the data points within the stream of data points do not require to be equally spaced. Employing the verifying step guarantees that data points may be available without large gaps, thus, providing for a nearly real-time reporting. Consequently, it may be feasible to adjust the standard sampling rate with an interval Δt slower than a sampling rate the apparatus could technically provide. This embodiment may particularly allow to minimize the power consumption of the apparatus as well as the exposure of the sensor undisturbed by the measurement means, such as an impinging the sensor with radiation which both may improve the lifetime of the apparatus.

Summarizing the findings of the present invention, the following embodiments are preferred:

Embodiment 1: A method for determining at least one smoothed data point $(t_k, s_k)$ within a stream of data points $\{t_i, s_i\}$ with $1 \leq i \leq z$, $k < z$, wherein i, z, and k are integers, wherein the stream of data points $\{t_i, s_i\}$ is consecutively acquired in a manner that a data point $(t_i, s_i)$ is acquired, preferably after a time interval Δt, after an acquisition of a preceding data point $(t_{i-1}, s_{i-1})$, wherein each data point $(t_i, s_i)$ in the stream of data points $\{t_i, s_i\}$ either comprises a valid value for a signal $s_i$ at a time $t_i$, wherein the valid value for the signal $s_i$ is recorded at the time $t_i$, or an invalid value for the signal $s_i$ at the time $t_i$, wherein the invalid value for the signal $s_i$ is recorded at the time $t_i$ and considered as invalid, or a missing value for the signal $s_i$ at the time $t_i$, wherein the missing value for the signal $s_i$ is missing at an expected time $t_i$, wherein the signal $s_i$ at the time $t_i$ comprises physical, chemical, biological, environmental, and/or technical data acquired by means of a technical set-up, wherein the method comprises the following steps:

a) Providing a set of data points which comprises the stream of data points $\{t_i, s_i\}$ with $1 \leq i \leq z$, $k \leq z$ or a specific set which is selected from the stream of data points $\{t_i, s_i\}$ or from a set of smoothed data points $\{t_k, s_k\}$;

b) For each smoothed data point $(t_k, s_k)$, creating a smoothing set, wherein the smoothing set comprises a subset of data points $\{t_\ell, S\ell\}$, wherein the subset of data points $\{t_\ell, t_\ell\}$ is taken from the set of data points provided during the preceding step with $$(k+\text{offset}-\text{smoothing window}+1) < \ell < (k+\text{offset}), \quad (1)$$

wherein offset>0 is a numerical value which comprises an offset number which defines a number of data points $(t_i, s_i)$ with $t_i > t_k$ which are acquired prior to creating the smoothing set for the data point $(t_k, s_k)$ and which comprise a valid value, and wherein the smoothing window is a numerical value which defines a length of the smoothing set;

c) For each smoothed data point $(t_k, s_k)$, verifying whether a first condition is fulfilled, wherein the first condition requires that in each pair of two adjacent data points $\{(t_{\ell-1}, S\ell_{-1}), (t_\ell, S\ell)\}$ in the smoothing set the condition $$(t_\ell - S\ell) \leq \text{gap length} \quad (2)$$

is fulfilled, wherein gap length is a numerical value which defines a maximum time difference which is admitted between the two adjacent data points within the smoothing set; if the first condition is not fulfilled for a certain $\ell_0$, the data points $(t_\ell, S\ell)$ with $\ell < \ell_0$ are removed from the smoothing set;

d) For each smoothed data point $(t_k, s_k)$, verifying whether a second condition is fulfilled, wherein the second condition requires that a numerical value n equals at least a numerical value minimal window, wherein n is a numerical value which equals a number of data points which remain in the smoothing set $\{\ell\}$ after the preceding step, wherein minimal window is a numerical value which equals a number of data points which are required to remain in the smoothing set $\{t_\ell, S\ell\}$ after the preceding step; if the second condition is not fulfilled, no value for the smoothed data point $(t_k, s_k)$ is determined and no smoothed data point $(t_k, s_k)$ or an error flag is returned; if the second condition is fulfilled, proceeding with the subsequent step;

e) For each smoothed data point $(t_k, s_k)$, calculating a slope set $\{t_\ell, S\ell'\}$ corresponding to the smoothing set with $1 \leq \ell \leq n$;

f) For each smoothed data point $(t_k, s_k)$, applying at least one exponential smoothing step to the slope set $\{t_\ell, S\ell'\}$, in which course an at least once modified slope set $\{t_\ell, S\ell'^*\}$ is determined;

g) For each smoothed data point $(t_k, s_k)$, integrating the at least once modified slope set $\{t_\ell, S\ell'^*\}$ determined in the preceding step, in which course the value for the smoothed data point $(t_k, s_k)$ is determined and returned; wherein prior to step b) for each data point in the set of data points provided according to step a), and/or after step b) for each data point provided in the smoothing set according to step b), a criterion is applied in a verifying step to the data point to deciding whether the data point is retained or discarded.

Embodiment 2: The method according to the preceding embodiment, wherein the criterion comprises the verifying step whether the data point $(t_j, s_j)$ comprises a valid value, or an invalid value, or a missing value, wherein the data point $(t_j, s_j)$ which comprises a valid value is retained, where the data point $(t_j, s_j)$ which comprises one of an invalid value or a missing value is discarded.

Embodiment 3: The method according to any one of the preceding embodiments, wherein an additional condition is verified whether at least one data point with a valid value exists in an offset or, preferably, whether all data points in the offset comprise a valid value, wherein the offset comprises offset number of data points $(t_i, s_i)$ with $t_i > t_k$ acquired ahead of the smoothed data point $(t_k, s_k)$ for which step b) is currently performed, after having removed a number of data points from the smoothing set during the verifying step; if the additional condition is not fulfilled, no value for the smoothed data point $(t_k, s_k)$ is determined and no smoothed data point $(t_k, s_k)$ or an error flag is returned.

Embodiment 4: The method according to any one of the preceding embodiments, wherein the numerical value offset is chosen from an interval [1, 4], whereby 2 is the preferred value.

Embodiment 5: The method according to any one of the preceding embodiments, wherein the numerical value smoothing window is chosen from an interval [7, 40], preferably from an interval [15, 25], whereby 20 is the most preferred value.

Embodiment 6: The method according to any one of the preceding embodiments, wherein the numerical value gap length is chosen from an interval [5 $\Delta t$, 30 $\Delta t$], preferably from an interval [5 $\Delta t$, 15 $\Delta t$], whereby 6 $\Delta t$ is the most preferred value.

Embodiment 7: The method according to any one of the preceding embodiments, wherein the numerical value minimal window is chosen from an interval [5, 20], preferably from an interval [5, 10], whereby 5 is the most preferred value.

Embodiment 8: The method according to any one of the preceding embodiments, wherein the specific set provided in step a) is selected by taking every p-th item, whereby p is a numerical value preferably chosen from an interval [2, 6], whereby 3 is the most preferred value.

Embodiment 9: The method according to the preceding embodiment, wherein p subsets are selected, whereby the q-th subset comprises a number of items q, p+q, 2p+q, . . . with q≤p, as long as the item comprises a value which is valid.

Embodiment 10: The method according to the preceding embodiment, wherein the p subsets are merged after smoothing.

Embodiment 11: The method according to the preceding embodiment, wherein the p subsets are merged after applying calculating means of corresponding items within the p subsets.

Embodiment 12: The method according to any one of the preceding embodiments, wherein the data point $(t_i, s_i)$ is acquired at a point of time $t_i$ which is prior to the end of the specific time interval $\Delta t = (t_i - t_{i-1})$.

Embodiment 13: The method according to the preceding embodiment, wherein the data point $(t_i, s_i)$ is acquired at a point of time $t_i$ which is prior to the end of the specific time interval $\Delta t = (t_i - t_{i-1})$ after the preceding data point $(t_{i-1}, s_{i-1})$ comprises a value which is invalid or missing.

Embodiment 14: The method according to any one of the an one of the preceding embodiments, wherein the specific set is selected by retaining items at data points with $t_0$, $t_0 + r\Delta t$, to $+2r\Delta t$, . . . with 0<r, or an adjacent item.

Embodiment 15: The method according to the preceding embodiment, wherein the adjacent item is at a distance of $\pm \Delta t$ or of $\pm 2 \Delta t$ from the data point $(t_i, s_i)$ which comprises a value which is invalid or missing.

Embodiment 16: The method according to any one of the preceding embodiments, wherein step e) comprises the following sub-steps:
e1) Defining a numerical value SlopeRange as a number of data points employed to calculate a slope of each data point ($t_\ell$, $S_\ell$);
e2) Assign a differentiation set $\{t_m, s_m\}$ to each data point ($t_\ell$, $S_\ell$), using the following procedure:
If SlopeRange is an odd number, selecting (SlopeRange−1)/2 data points before and (SlopeRange−1)/2 data points after each data point ($t_\ell$, $S_\ell$), as long as the selected data points exist in the smoothing set; if a data point ($t_\ell$, $S_\ell$) does not exist at an end of the smoothing set, working with the data points which do exist;
if SlopeRange is an even number, selecting SlopeRange/2 data points before and (SlopeRange/2−1) data points after each data point ($t_\ell$, $S_\ell$), as long as the selected data points exist in the smoothing set; if a data point ($t_\ell$, $S_\ell$) does not exist at an end of the smoothing set, working with the data points which do exist;
e3) Calculating the slope set $\{t_\ell, S_\ell'\}$ corresponding to the smoothing set according to the formula $$s'_\ell = \frac{d \sum_{m=1}^{d} t_m s_m - \sum_{m=1}^{d} t_m \sum_{m=1}^{d} s_m}{d \sum_{m=1}^{d} t_m^2 - \sum_{m=1}^{d} t_m \sum_{m=1}^{d} t_m} \quad (3)$$

where the sums $\Sigma$ are calculated over the data points in the differentiation set $\{t_m, s_m\}$ with d either being equal to SlopeRange or smaller if data points did not exist at the ends of the smoothing set, and the calculation is performed for each point in the smoothing set, $1 \leq \ell \leq n$.

Embodiment 17: The method according to the preceding embodiment, wherein the numerical value SlopeRange is chosen from an interval [3, 6], whereby 3 is the preferred value.

Embodiment 18: The method according to any one of the preceding embodiments, wherein step f) comprises the following sub-steps:
f1) Applying a first forward exponential smoothing to the slope set $\{t_\ell, S_\ell'\}$ acquired in step e) in an ascending order 1, 2, . . . , n−1, n with $s_1'^* = s_1'$ and $S_\ell'^* = W_{f1} \cdot S_\ell' + (1 - W_{f1}) \cdot S_{\ell-1}'^*$ for $1 < \ell \leq n$,  (4)

wherein $W_{f1}$ is a first weight adapted for the first forward exponential smoothing;
f2) Applying a reverse exponential smoothing to the slope set $\{t_\ell, S_\ell'^*\}$ modified in the preceding sub-step in a descending order n, n−1, . . . , 2, 1 with $s_n'^{**} = s_n'^*$ and $S_\ell'^{**} = W_r \cdot S_\ell'^* + (1 - W_r) \cdot S_{\ell+1}'^{**}$ for $1 \leq \ell < n$,  (5)

wherein $W_r$ is a second weight adapted for the reverse exponential smoothing;
f3) Applying a second forward exponential smoothing to the slope set $\{t_\ell, S_\ell'^*\}$ modified in the preceding sub-step in an ascending order 1, 2, . . . , n with $s_1'^{*} = s_1'^{}$ and $S_\ell'^{*} = W_{f2} \cdot S_\ell'^{} + (1 - W_{f2}) \cdot S_{\ell-1}'^{***}$ for $1 < \ell \leq n$,  (6)

wherein $W_{f2}$ is a third weight adapted for the second forward exponential smoothing.

Embodiment 19: The method according to the preceding embodiment, wherein the first weight adapted for the first forward exponential smoothing $W_{f1}$ is chosen from an interval [0.3, 0.6], whereby 0.5 is the preferred value.

Embodiment 21: The method according to any one of the two preceding embodiments, wherein the second weight adapted for the reverse exponential smoothing $W_r$ is chosen from an interval [0.2, 0.5], whereby 0.33 is the preferred value.

Embodiment 22: The method according to any one of the three preceding embodiments, wherein the third weight adapted for the second forward exponential smoothing $W_{f2}$ is chosen from an interval [0.3, 0.6], whereby 0.5 is the preferred value.

Embodiment 23: The method according to any one of the preceding embodiments, wherein step g) comprises the following sub-steps:

g1) Calculating an average orig mean of the values $S\ell$ with $1 \le \ell \le n$ within the smoothing set prior to step e);

g2) Numerically integrating the at least once modified slope set ($t\ell$, $S\ell'^*$) with integral$_1$=0 and $$\text{integra } l\ell = \text{integra } l\ell_{-1} + \{(1-w_i) \cdot S\ell' + w_i \cdot S\ell_{-1}'^*\} \cdot \{t\ell - t\ell_{-1}\} \text{ for } 1 < \ell < n, \quad (7)$$

wherein $w_i$ is a fourth weight adapted for integrating; thereby creating an integrated set;

g3) Calculating an average new mean of the values integral$_i$, with $1 \le i \le n$ within the integrated set;

g4) Calculating an integration constant int const by applying a formula $$\text{int const} = \text{orig mean} - \text{new mean}; \quad (8)$$

g5) Calculating the smoothed value of $$s_k = \text{integral}_k + \text{int const} \quad (9)$$

and return the value for the smoothed data point ($t_k$, $s_k$) with k=n−offset.

Embodiment 24: The method according to the preceding embodiment, wherein the fourth weight adapted for integrating $w_i$ is chosen from an interval [0.25, 0.75], whereby 0.33 is the preferred value.

Embodiment 25: The method according to any one of the preceding embodiments, wherein at least one triple data point ($t_k$, $s_k$, $s_k'$) is returned, wherein the triple data point ($t_k$, $s_k$, $s_k'$) includes a value $s_k'$ for the slope f the smoothed value $s_k$.

Embodiment 26: The method according to any one of the preceding embodiments, wherein the stream of data points $\{t_i, s_i\}$ comprises a measurement series which is consecutively recorded by a sensor, wherein the sensor is adapted for recording the signal $s_i$ at the time $t_i$.

Embodiment 27: The method according to the preceding embodiment, wherein the signal $s_i$ at the time $t_i$ is particularly related to a concentration of a substance in a volume.

Embodiment 28: The method according to any one of the two preceding embodiments, wherein the sensor is an optical sensor.

Embodiment 29: The method according to the preceding embodiment, wherein the sensor is a fluorescence sensor, Embodiment 30: The method according to any one of the four preceding embodiments, wherein the sensor is adapted for determining a glucose concentration in a body fluid.

Embodiment 31: The method according to the preceding embodiment, wherein the sensor is adapted for determining a glucose concentration in an interstitial fluid.

Embodiment 32: An apparatus for determining at least one smoothed data point ($t_k$, $s_k$) within a stream of data points $\{t_i, s_i\}$ with $1 \le i$, $k \le m$, comprising an instruction device for instructing a sensor to record a series of signals $s_i$ at a time $t_i$ and to deliver a stream of data points $\{t_i, s_i\}$, wherein the signal $s_i$ at the time $t_i$ comprises physical, chemical, biological, environmental, and/or technical data acquired by means of a technical set-up, wherein at least some of the data points ($t_i$, $s_i$) in the stream of data points $\{t_i, s_i\}$ comprise a valid value for the signal $s_i$ at the time $t_i$;

a receiving and storing device for receiving and subsequently storing the stream of data points $\{t_i, s_i\}$;

a calculating device for determining the at least one smoothed data point ($t_k$, $s_k$) within the stream of data points $\{t_i, s_i\}$ with $1 \le i \le m$, which are configured to perform any steps according to any of the preceding embodiments.

Embodiment 33: The apparatus according to the preceding embodiment, wherein the apparatus is an analytical device for determining at least one body function of a user, further comprising at least one sensor for recording at least one body function of the user.

Embodiment 34: The apparatus according to the preceding embodiment, wherein the at least one sensor is selected from the group consisting of: a sensor for measuring an analyte concentration of at least one analyte in a body tissue or a body fluid of the user; a cardiac sensor for determining at least one cardiac function of the user; a pulse sensor; a blood pressure sensor; an ECG; an EEG.

Embodiment 35: The apparatus according to any one of the preceding embodiments, wherein the apparatus is separated into at least two separate parts, wherein the instruction device is coupled to the sensor, wherein the instruction device comprises a wireless sending device, and wherein the receiving and storing device and the calculating device are coupled together.

Embodiment 36: A use of the apparatus according to any one of the preceding embodiments referring to an apparatus for a purpose, selected from the group consisting of: measuring an analyte concentration of at least one analyte in a body tissue or a body fluid of the user; determining at least one cardiac function of the user; determining a pulse of the user; determining a blood pressure of the user; recording an ECG; recording an EEG.

Embodiment 37: A computer program including computer-executable instructions for performing the method according to any one of the preceding method claims, when the program is executed on a computer or computer network.

Embodiment 38: A data carrier having a data structure stored thereon, wherein the data structure, after loading into a computer or computer network, is capable of executing the method according to any one of the preceding method claims.

Embodiment 39: A computer or computer network comprising at least one processor, wherein the processor is adapted to perform the method according to any one of the preceding embodiments referring to a method.

Embodiment 40: A computer loadable data structure that is adapted to perform the method according to any one of the preceding embodiments referring to a method while the data structure is being executed on a computer.

Embodiment 41: A computer program, wherein the computer program is adapted to perform the method according to any one of the preceding embodiments referring to a method while the program is being executed on a computer.

Embodiment 42: A computer program comprising program means for performing the method according to any one of the preceding embodiments referring to a method while the computer program is being executed on a computer or on a computer network.

Embodiment 43: A computer program comprising program means according to the preceding embodiment, wherein the program means are stored on a storage medium readable to a computer.

Embodiment 44: A storage medium, wherein a data structure is stored on the storage medium and wherein the data structure is adapted to perform the method according to any one of the preceding embodiments referring to a method after having been loaded into a main and/or working storage of a computer or of a computer network Embodiment 45: A computer program product having program code means, wherein the program code means can be stored or are stored on a storage medium, for performing the method according to any one of the preceding embodiments referring to a method, if the program code means are executed on a computer or on a computer network.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

Figure 2:
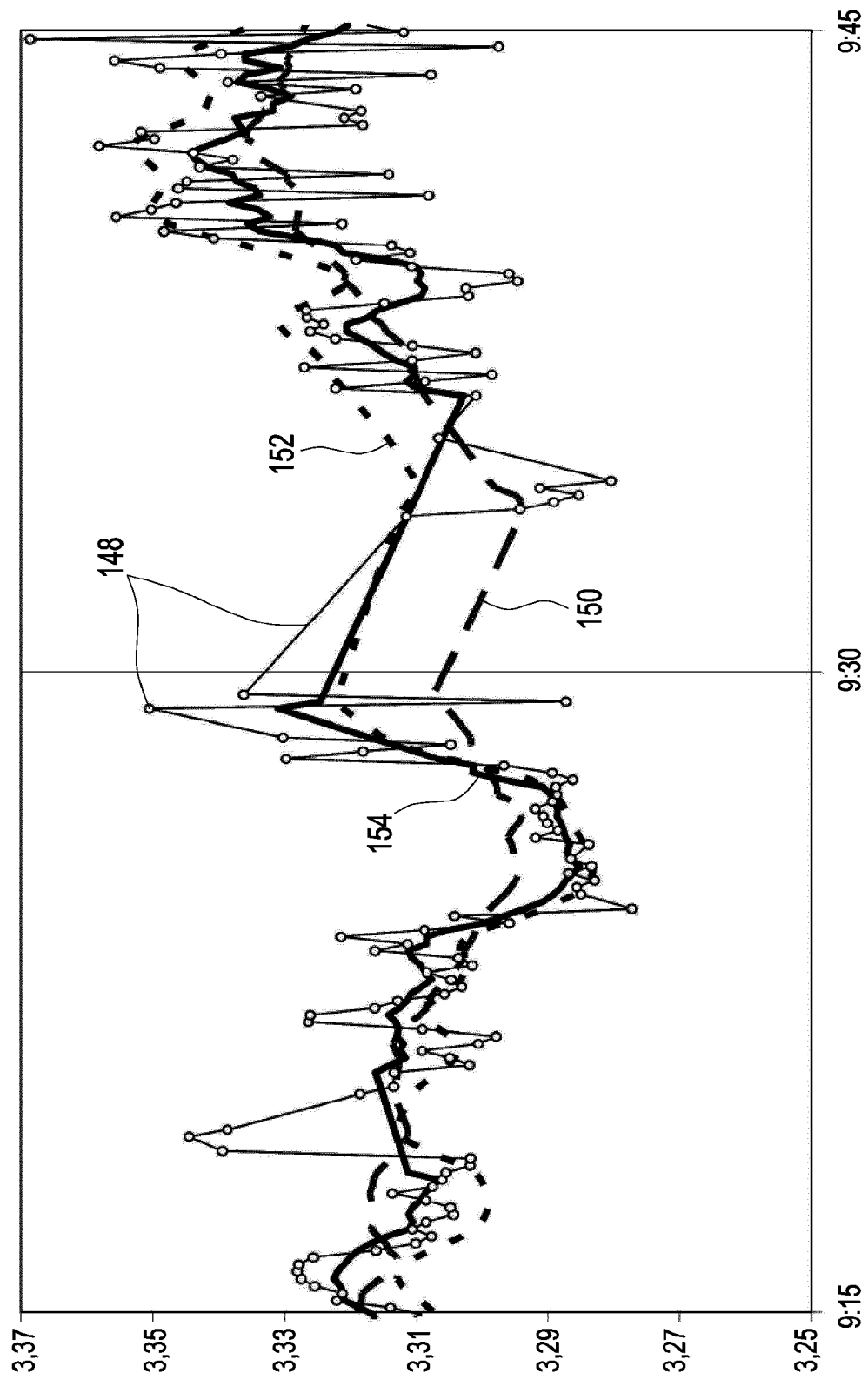
Figure 2:
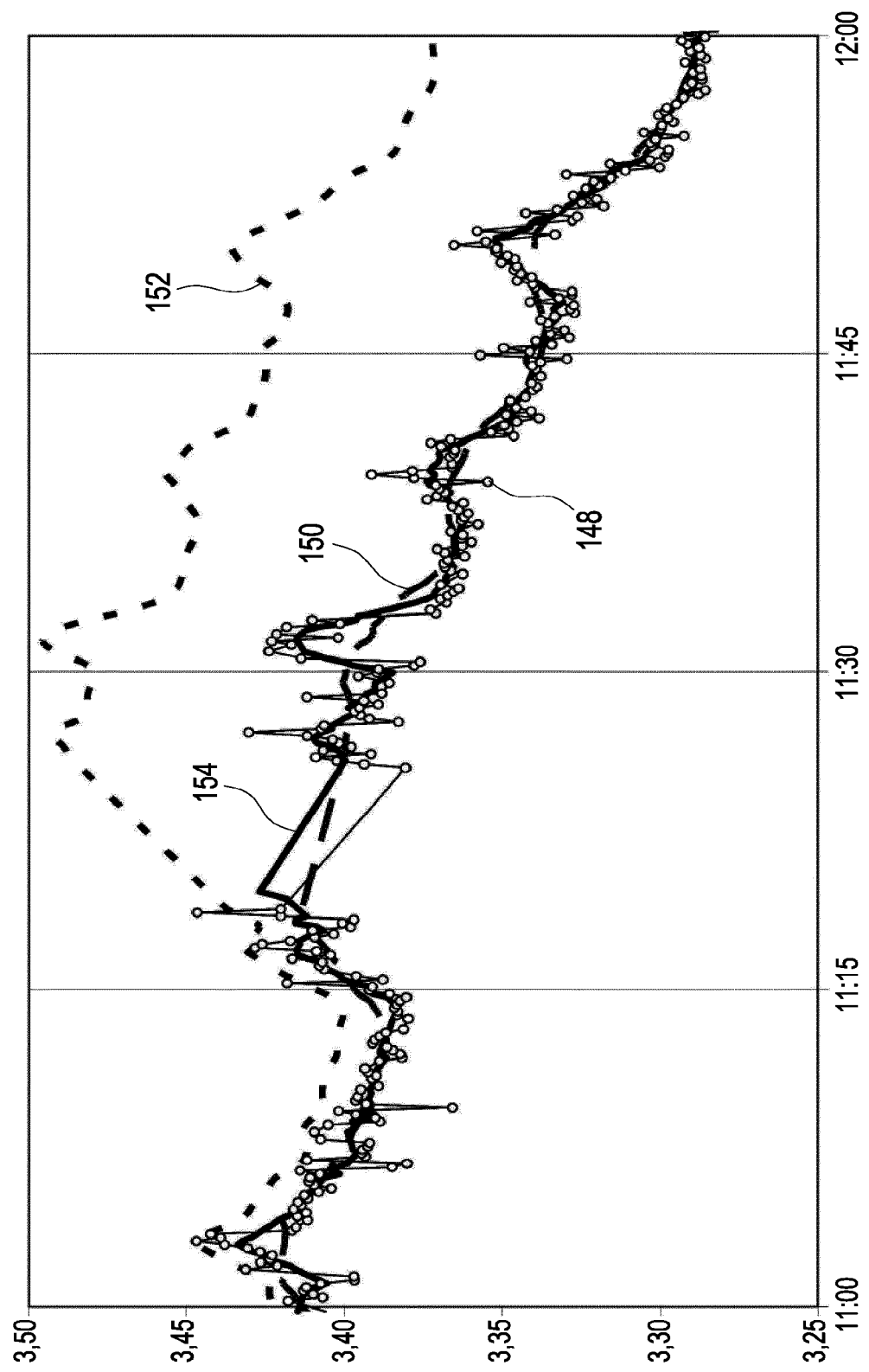
Figure 3:
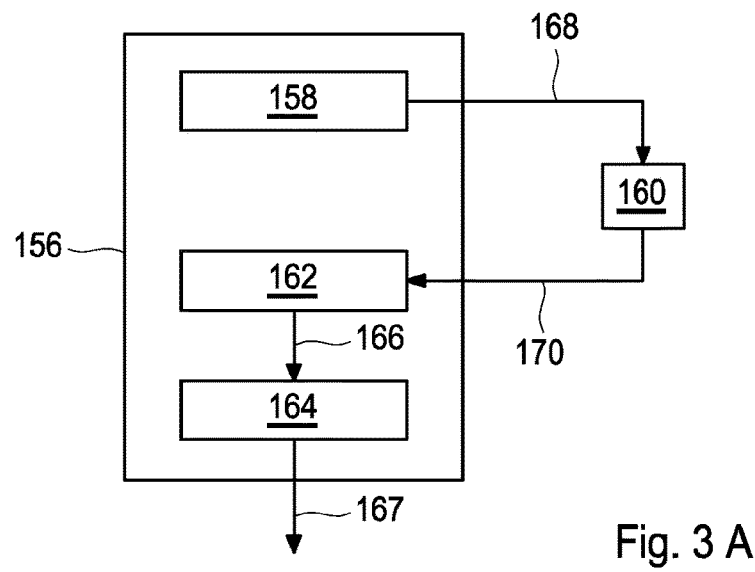
Figure 3:
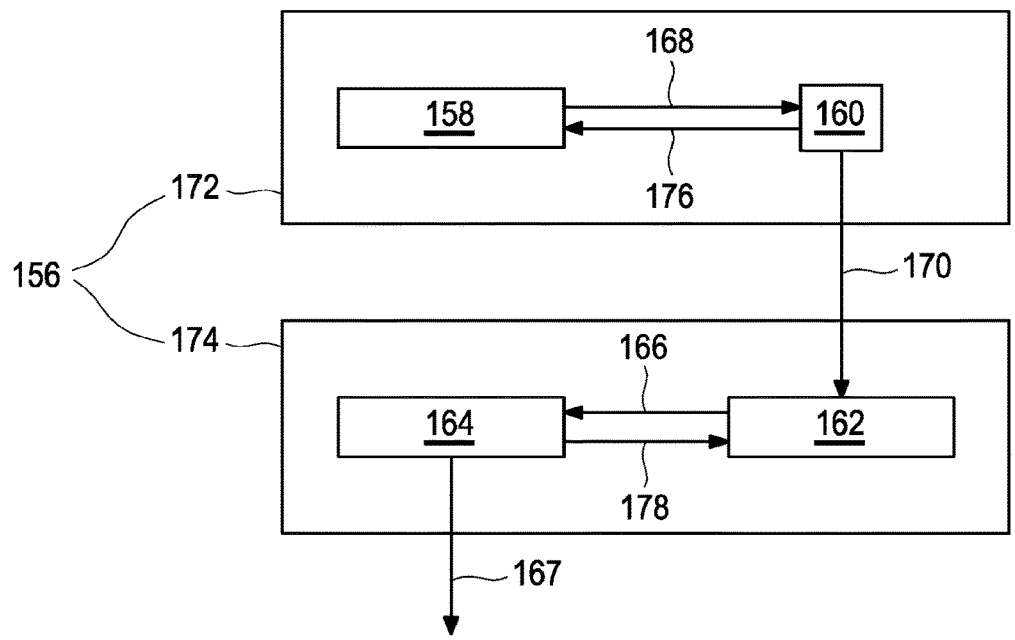

In the Figures:

FIG. 1 presents a schematic overview over a preferred embodiment according to the method for determining at least one smoothed data point within a stream of data points;

FIGS. 2A-B show a comparison for a stream of data points with a gap of 25 data points (FIG. 2A), and a gap of 42 data points (FIG. 2B), respectively, as presented in a first set of original raw data points, in a second and a third set of data points which are smoothed according to methods known from the state of the art, and in a fourth set of data points which are smoothed according to the present method; and FIGS. 3A-B schematically depict two different embodiments (FIGS. 3A and 3B) of an apparatus for determining at least one smoothed data point within a stream of data points.

DETAILED DESCRIPTION OF THE EMBODIMENTS

FIG. 1 presents a schematic overview over a preferred embodiment according to the method for determining at least one smoothed data point $(t_k, s_k)$ within a stream of data points $\{t_i, s_i\}$ 110 with $1 \leq i \leq z$, $k<z$, wherein i, z, and k are integers. Herein, a signal $s_i$ at a time $t_i$ 112 comprises physical, chemical, biological, environmental, and/or technical data acquired by means of a technical set-up. Within this regard, the stream of data points 110 may be consecutively acquired over the time 112 in a manner that a previous data point may be recorded at an earlier time 114 whereas the latest data point 116 may be reported near the actual reporting time 112. By going back in time from the latest data point 116 by a number of points equal to Smoothing Window 118, a smoothing set 120 may be created. Hereby, an offset 119, which describes the difference between the latest data point 116 and the actual reporting time 112, occurs. In a subsequent verifying step 122, data points which comprise an invalid value or a missing value may be removed from the smoothing set 120. The method as presented in FIG. 1 may comprise an additional condition 124 which may examine whether any data still exist in the offset 119 after having removed a number of data points from the smoothing set 120 during the verifying step 122. If the additional condition 124 is not fulfilled, no output will be available from the recorded stream of data points. In this case, a waiting step 126 may be introduced, where the further performance of the method may pause until a recording of the next data point may occur. As soon as the next data point may be available, the smoothing set 120 may be moved in a sliding step 128 to the right into a position where the latest data point 116 is located. From the latest data point 116 it may then be feasible to restart the method with creating a new smoothing set 120 from the accordingly adjusted Smoothing Window 118.

On the other hand, if data exist in the offset 119 according to the additional condition 124, it may then be verified whether a first condition 130, which may examine whether there are large gaps within the smoothing set 120, may be fulfilled or not. If the first condition 130 is fulfilled, trailing data may be removed from the smoothing set 120. Subsequently, it may be examined whether a second condition 132, which may verify whether the smoothing set may be long enough for a further performing of the method according to the invention, may be fulfilled. If the second condition 132 may be not fulfilled, the same consequence as described above when no data did exist in the offset 118 may occur. Consequently a waiting step 126 may be performed in this case until the next data point may be available, on which event the sliding step 128 may be performed as described above.

On the other hand, when the smoothing set may be examined by verifying the second condition 132 to be long enough, a first calculating step 134 may be performed, wherein the parameter orig mean within the smoothing set 120 is determined. Subsequently, in a second calculating step 136 an initial slope set may be calculated for the data points in the smoothing set 120, on which a first forward smoothing step 138 may be applied, followed by a reverse smoothing step 140, and, subsequently, by a second forward smoothing step 142. During the smoothing steps 138, 140, 142 the slope set may such be modified three times, wherein the finally modified slope set may be employed as an input for an integrating step 144, in which course a value for the smoothed data point is determined and returned in a determining and returning step 146.

Having finished such a single performance with the latest data point 116 as input, the method may terminate. Alternatively, the method may continue with a subsequent pass as soon as the next data point may be available and the smoothing set may be moved to the right according to the sliding step 128 in order to cover the latest data point 116.

In the following a number of specific embodiments will be described which may be selected due to a specific requirement with regard to the time series data.

A first embodiment which could be designated as a "one-pass real-time smoothing", therefore, employs the steps as presented in FIG. 1 and the respective description together with parameters which are selected from the range and/or values as given in Table 1.

A second embodiment, which could be designated as a "two-pass real-time smoothing with data reduction" may be selected in a case where a better smoothing is required while reporting in real-time or nearly real-time is still needed. In this case, the method as presented schematically in FIG. 1 may be applied twice in the following manner. First, the method as presented in FIG. 1 may be applied in a first pass to the original data set with parameters taken from Table 1. Thereafter, only every p-th data point in the data set resulting from the determining and returning step 146 may be retained while discarding the rest of the data points, wherein a typical value for p may be selected to be equal to 3. Thereby, a reduced data set may be obtained. Then, the method as depicted in FIG. 1 may be applied in a second pass to the reduced data set, particularly with the same parameters as used in the first pass. Alternatively, it may be possible to employ differing parameters, either selected from Table 1 or not, for the second pass compared with the first pass.

As a variation of the second embodiment, p data sets may be created from the original data set, wherein the first of these data sets may start with the data points 1, 1+p, 1+2p, . . . whereas the second data set may start with 2, 2+p, 2+2p, . . . etc. Thereafter, the method as presented in FIG. 1 is applied to each of the p data sets, by which p smoothed data sets may be obtained. Subsequently, the p smoothed data sets may be merged either without further processing, or, preferably, after applying calculating means of corresponding items within the p subsets. Hereby, the calculating means may be selected from arithmetic means, medians or other such calculations, which may be applied to the respective data points either in a direct manner, resulting in a reduced number of data points compared to the input data set, or in a sliding manner, resulting in the same number of data points compared to the input data set. In addition, data points may be eliminated according to any criterion before calculating means.

In a third embodiment, which may be designated as a "real-time smoothing on a preprocessed reduced data set", the method as shown in FIG. 1 may be applied to a reduced data set. The reduced data set may be prepared from the original data set by retaining only every p-th data point or by retaining items at such data points which are recorded at times $t_0$, $t_0+r\cdot\Delta t$, $t_0+2r\cdot\Delta t$, . . . with $0<r$, r being an integer. In case such a selected item turns out to be an invalid value or a missing value, an adjacent item, in particular wherein the adjacent item is at a distance of $\pm\Delta t$ or $\pm 2\cdot\Delta t$ from the respective data point, may be selected. Hereby, a number of attempts for searching a valid data point backward and/or forward may be chosen appropriately as long as any point may not be used twice. Thereafter, the method which is depicted in FIG. 1 may be applied to the reduced data set with parameters selected from Table 1.

A similar variation as applied to the second embodiment may mutatis mutandis be also applied to the third embodiment. In this manner, it may also be feasible within the third embodiment to create p data sets which are used as an input for the method according to FIG. 1, wherein the resulting smoothed data sets may be merged in one of the manners as described above.

Whereas the first embodiment may provide a good smoothing on short time scales, it has been found that the method according to the second and/or the third embodiment may be particular useful for smoothing noise on longer times scales. Whereas the second embodiment may often provide a better smoothing compared to the method according to the third embodiment, the second embodiment may computationally be more demanding and requires more data points in the future. Consequently, the method according to the second embodiment may not return a smoothed data point as early as a data point which may have been smoothed by a method according to the third embodiment. The above specified variations to the second embodiment and/or to the third embodiment, however, may demand more computational time and effort and, therefore, may be only suitable in a case where an additional smoothing and/or a tight spacing of the data points over the time may be required.

The variations of the second and third embodiment may particularly be advantageous when an output in form of a triple comprising the slope, $(t_k, s_k, s_k')$ is desired. Hereby, the calculating means for merging the subset are particularly adapted to result in a smooth value for the slope $s_k'$.

As a practical example, the method according to the present invention has been applied on the data points which were acquired during a clinical study which comprised 20 sensors in a cohort of ten patients and up to six streams of data points per sensor. As a result, it could be proved that by an application of the method according to the present invention data are recorded that show less distortion and approximately equal noise compared to data acquired with a sliding average as used before. In addition, the present method allowed to calculate a slope of the signal and, thus, to provide the data in a manner that a numerical correction for deviations which are caused by glucose dynamics could be applied. Over the whole cohort, the methods according to the second embodiment and to the third embodiment have been compared with a nearly identical result. An important parameter adapted to compare such kinds of results is the "mean absolute relative deviation" (MARD) which describes deviations from a reference value being expressed in a percent value, whereby the absolute value is taken and the mean is calculated over one set of data, for example one data stream of the sensor. As an example, it has been found that in a typical experiment the MARD value decreases from a mean over the whole cohort from 14.6% to 13.6% by the application of the method according to the present invention. With streams of data points which particularly comprise a lot of noise, the improvement was often found to be much better.

As an example, a reduction of the MARD value from 35% to 25% by the application of the method according to the invention could be observed in a particularly noisy data set. In addition to this statistical value which disregards any dynamics in the glucose values, less bias could be observed, particularly within dynamic regions.

The method according to the present invention is particularly suited to deal with large gaps which may occur in the stream of data points. FIGS. 2A and 2B show two examples in which there are large gaps in the data stream. In FIG. 2A, a gap of 25 data points occurs, whereas in FIG. 2B even 42 data points exhibit a missing value. In both FIGS. 2A and 2B, the original raw data 148 as obtained from the sensor which may be located within the technical set-up are presented together with the smoothed data points, which are smoothed according to the state of the art either with a symmetric moving average 150 over 30 data points or with the so-called "reverse smoothing" method 152 according to Roark, as well as smoothed data points 154 returned by the method according to the present invention. A comparison between the sets of the smoothed data 150, 152 smoothed according to the state of the art and the set of smoothed data 154 smoothed according to the present invention shows that the method proposed here is far more capable of dealing with large gaps within the stream of data points than the "reverse smoothing" method 152, and comparable to the symmetric moving average 150 which requires 15 data points in the future. This feature is of particular importance in the case of real-time or nearly real-time acquisition and smoothing of data points.

FIGS. 3A and 3B schematically display two embodiments of an apparatus 156 which is adapted to determining at least one smoothed data point within a stream of data points.

According to the embodiment shown in FIG. 3A, the apparatus 156 comprises an instruction device 158 for instructing a sensor 160 to record a series of signals $s_i$ in a time $t_i$ and to deliver a stream of data points $\{t_i, s_i\}$ with $1 \leq i \leq z$ to a receiving and storing device 162 which is also comprised within the apparatus 156. The apparatus 156 further comprises a calculating device 164 which receives the stream of data points by means of a first connecting device 166 from the receiving and storing device 162, wherein the calculating device 164 is configured to determining the at least one smoothed data point $(t_k, s_k)$ with $k < z$ within the stream of data points, wherein the at least one smoothed data point $(t_k, s_k)$ may be provided by an output 167 for any further purpose. Hereby, the instruction device 158 may comprise a sending device 168 which is configured for forwarding instructions wire-bound and/or wireless to the sensor 160, whereas the receiving and storing device 162 may comprise a receiving device 170 which is configured for receiving the stream of data points $\{t_i, s_i\}$ wire-bound and/or wireless from the sensor 160. In this specific example as depicted in FIG. 3A, the sensor 160 does not form a constituent part of the apparatus 156. However, other embodiments may be feasible, in particular, wherein the sensor 160 may, nevertheless, constitute an integral part of the apparatus 156.

FIG. 3B shows a particularly preferred embodiment, wherein the apparatus 156 may be mechanically and/or physically separated into a first part 172 and into a second part 174. Hereby, the instruction device 158 may together with the sensor 160 be located within the first part 172 of the apparatus 156, wherein the first part 172 of the apparatus 156 may, by way of example, be worn on or near the human body, where the sensor 160 may be applied. For this purpose, the instruction device 158 may comprise a wire-bound sending device 166 configured to forward instructions to the sensor 160, wherein the sensor 160 may comprise a wire-bound transfer device 176 configured for transferring data to the instruction device 158. This preferred arrangement may particularly allow to realize a preferred function which comprises that a data point $(t_i, s_i)$ may be acquired prior to the end of a specific time interval $\Delta t = (t_i - t_{i-1})$, in particular in a case wherein the preceding data point $(t_{i-1}, s_{i-1})$ may comprise a value which is either invalid or missing. However, other types of connections between the instruction device 158 and the sensor 160 may also be possible.

In addition, both the receiving and storing device 162 as well as the calculating device 164 may be located within the second part 174 of the apparatus 156 and may be coupled together, for example as a part of an ASIC, and, by way of example, may be carried by the user or may be left under supervision of a nursing staff. Hereby, it is particularly preferred when the calculating device 164 receives the stream of data points by $\{t_i, s_i\}$ means of a first connecting device 166 from the receiving and storing device 162 and may, additionally, be configured for forwarding intermediate values to the receiving and storing device 162 by means of a second connecting device 178. Also in this embodiment, the calculating device 164 may be configured for providing the at least one smoothed data point $(t_k, s_k)$ for any purpose via the output 167. In this preferred embodiment, the receiving and storing device 162 may comprise a wireless receiving device 170 which is configured for receiving the stream of data points from the sensor 160. However, other types of connections between the receiving and storing device 162 and the calculating device 164 may also be possible. In addition, the receiving and storing device 162 may also be realized as at least two separate entities which might communicate with each other by various possible ways.

LIST OF REFERENCE NUMBERS 110 stream of data points
112 recording time
114 earlier data point
116 latest data point
118 smoothing window
119 offset
120 smoothing set
122 verifying step
124 additional condition
126 waiting step
128 sliding step
130 first condition
132 second condition
134 first calculating step
136 second calculating step
138 first forward smoothing step
140 reverse smoothing step
142 second forward smoothing step
144 integrating step
146 determining and returning step
148 set of original raw data
150 symmetric moving average over 30 points (state of the art)
152 set of smoothed data according to Roark (state of the art)
154 set of smoothed data according to the present invention
156 apparatus
158 instruction device
160 sensor
162 receiving and storing device
164 calculating device
166 first connecting device
167 output
168 sending device
170 receiving device
172 first part of the apparatus
174 second part of the apparatus
176 transfer device
178 second connecting device

The invention claimed is:

1. A method for glucose monitoring and treatment of a patient using a glucose monitoring apparatus, the method comprising:
capturing a stream of data points by a glucose monitor sensor of the glucose monitoring apparatus, wherein the stream of data points is based on a signal related to a glucose concentration of a body fluid of the patient;
receiving, by a processor of the glucose monitoring apparatus, a set of data points selected from the stream of data points;
generating, by the processor, a smoothing set for each data point of the set of data points to be smoothed;
verifying, by the processor, whether a first condition has been fulfilled for each data point of the set of data points to be smoothed, wherein the first condition requires that in each pair of adjacent first and second data points of the smoothing set, a difference in measurement time between the adjacent first and second data points does not exceed a predefined gap length threshold;

removing, by the processor, each second data point that does not fulfill the first condition;

verifying, by the processor, whether a second condition has been fulfilled for each data point of the set of data points to be smoothed, wherein the second condition requires that at least a threshold number of data points remain after removal of each second data point that does not fulfill the first condition;

calculating, by the processor, a slope set corresponding to the smoothing set for each data point to be smoothed in response to determining that the second condition has been fulfilled;

applying, by the processor, at least one exponential smoothing to the slope set to generate an at least once modified slope set for each data point to be smoothed;

determining, by the processor, a corresponding smoothed value for each data point to be smoothed by integrating the at least once modified slope set for each data point to be smoothed; and treating the patient based on the corresponding smoothed value for each data point to be smoothed.

2. The method of claim 1, wherein the signal comprises a measured amplitude of at least one of a voltage or current related to the glucose concentration of the body fluid.

3. The method of claim 1, wherein applying the at least one exponential smoothing to the slope set comprises performing a first forward exponential smoothing to the slope set based on a first weight.

4. The method of claim 3, wherein applying the at least one exponential smoothing to the slope set further comprises performing a reverse exponential smoothing to the slope set based on a second weight in response to performing the first forward exponential smoothing.

5. The method of claim 4, wherein applying the at least one exponential smoothing to the slope set further comprises performing a second forward exponential smoothing to the slope set based on a third weight in response to performing the reverse exponential smoothing.

6. The method of claim 1, wherein receiving the set of data points selected from the stream of data points comprises receiving the set of data points in real time relative to capturing the stream of data points by the glucose monitor sensor.

7. The method of claim 1, wherein receiving the set of data points selected from the stream of data points comprises wirelessly receiving at least one of the signal or the stream of data points from the glucose monitoring sensor.

8. The method of claim 1, wherein the glucose monitoring sensor comprises an optical sensor.

9. The method of claim 1, wherein the body fluid comprises an interstitial fluid of the patient.

10. A glucose monitoring apparatus, comprising:
a glucose monitoring sensor configured to capture a stream of data points, wherein the stream of data points is based on a signal related to a glucose concentration of a body fluid of the patient;
a processor; and
a memory comprising a plurality of instructions stored thereon that, in response to execution by the processor, causes the processor to:
receive a set of data points selected from the stream of data points;
generate a smoothing set for each data point of the set of data points to be smoothed;
verify whether a first condition has been fulfilled for each data point of the set of data points to be smoothed, wherein the first condition requires that in each pair of adjacent first and second data points of the smoothing set, a difference in measurement time between the adjacent first and second data points does not exceed a predefined gap length threshold;

remove each second data point that does not fulfill the first condition;

verify whether a second condition has been fulfilled for each data point of the set of data points to be smoothed, wherein the second condition requires that at least a threshold number of data points remain after removal of each second data point that does not fulfill the first condition;

calculate a slope set corresponding to the smoothing set for each data point to be smoothed in response to determining that the second condition has been fulfilled;

apply at least one exponential smoothing to the slope set to generate an at least once modified slope set for each data point to be smoothed; and determine a corresponding smoothed value for each data point to be smoothed by integrating the at least once modified slope set for each data point to be smoothed, wherein the corresponding smoothed value is associated with treatment of the patient.

11. The glucose monitoring apparatus of claim 10, further comprising:
a first part including the glucose monitoring sensor; and
a second part including the processor and physically separated from the first part.

12. The glucose monitoring apparatus of claim 11, wherein processor is configured to wirelessly receive at least one of the signal or the stream of data points from the glucose monitoring sensor.

13. The glucose monitoring apparatus of claim 10, wherein the glucose monitoring sensor comprises a fluorescence sensor.

14. The glucose monitoring apparatus of claim 10, wherein the body fluid comprises an interstitial fluid of the patient.

15. The glucose monitoring apparatus of claim 10, wherein the signal comprises a measured amplitude of at least one of a voltage or current related to the glucose concentration of the body fluid.

16. The glucose monitoring apparatus of claim 10, wherein to apply the at least one exponential smoothing to the slope set comprises to perform a first forward exponential smoothing to the slope set based on a first weight.

17. The glucose monitoring apparatus of claim 16, wherein to apply the at least one exponential smoothing to the slope set further comprises to:
perform a reverse exponential smoothing to the slope set based on a second weight in response to the first forward exponential smoothing; and
perform a second forward exponential smoothing to the slope set based on a third weight in response to the reverse exponential smoothing.

18. One or more non-transitory machine-readable storage media comprising a plurality of instructions stored thereon that, in response to execution by a processor, causes the processor to:
instruct a glucose monitoring sensor to capture a stream of data points, wherein the stream of data points is based on a signal related to a glucose concentration of a body fluid of a patient;
receive a set of data points selected from the stream of data points;

generate a smoothing set for each data point of the set of data points to be smoothed;

verify whether a first condition has been fulfilled for each data point of the set of data points to be smoothed, wherein the first condition requires that in each pair of adjacent first and second data points of the smoothing set, a difference in measurement time between the adjacent first and second data points does not exceed a predefined gap length threshold;

remove each second data point that does not fulfill the first condition;

verify whether a second condition has been fulfilled for each data point of the set of data points to be smoothed, wherein the second condition requires that at least a threshold number of data points remain after removal of each second data point that does not fulfill the first condition;

calculate a slope set corresponding to the smoothing set for each data point to be smoothed in response to determining that the second condition has been fulfilled;

apply at least one exponential smoothing to the slope set to generate an at least once modified slope set for each data point to be smoothed; and determine a corresponding smoothed value for each data point to be smoothed by integrating the at least once modified slope set for each data point to be smoothed, wherein the corresponding smoothed value is associated with treatment of the patient.

19. The one or more non-transitory machine-readable storage media of claim 18, wherein the signal comprises a measured amplitude of at least one of a voltage or current related to the glucose concentration of the body fluid.

20. The one or more non-transitory machine-readable storage media of claim 18, wherein to apply the at least one exponential smoothing to the slope set comprises to:

perform a first forward exponential smoothing to the slope set based on a first weight;

perform a reverse exponential smoothing to the slope set based on a second weight in response to the first forward exponential smoothing; and perform a second forward exponential smoothing to the slope set based on a third weight in response to the reverse exponential smoothing.

\* \* \* \* \*